(12) United States Patent
Wolfe et al.

(10) Patent No.: US 7,825,231 B2
(45) Date of Patent: Nov. 2, 2010

(54) METHOD OF AMIDATED PEPTIDE BIOSYNTHESIS AND DELIVERY IN VIVO: ENDORMORPHIN-2 FOR PAIN THERAPY

(75) Inventors: Darren P. Wolfe, 271 Hillary Dr., Verona, PA (US) 15147; Joseph C. Glorioso, 101 Hawthorne Rd., Fox Chapel, PA (US) 15238; David J. Fink, Ann Arbor, MI (US)

(73) Assignees: Darren P. Wolfe, Pittsburgh, PA (US); Joseph C. Glorioso, Pittsburgh, PA (US); Regents of the University of Michigan, Ann Arbor, MI (US)

( * ) Notice: Subject to any disclaimer, the term of this patent is extended or adjusted under 35 U.S.C. 154(b) by 611 days.

(21) Appl. No.: 11/445,837

(22) Filed: Jun. 1, 2006

(65) Prior Publication Data

US 2006/0281070 A1    Dec. 14, 2006

Related U.S. Application Data

(60) Provisional application No. 60/686,253, filed on Jun. 1, 2005.

(51) Int. Cl.
C07H 21/04 (2006.01)
A61K 31/711 (2006.01)
C12N 15/12 (2006.01)
C12N 15/62 (2006.01)

(52) U.S. Cl. .................. 536/23.4; 514/44 R; 435/320.1
(58) Field of Classification Search ........................ None
See application file for complete search history.

(56) References Cited

U.S. PATENT DOCUMENTS

| | | | |
|---|---|---|---|
| 4,350,764 A | 9/1982 | Baxter et al. |
| 4,468,383 A | 8/1984 | Rodbard et al. |
| 4,469,631 A | 9/1984 | Baxter et al. |
| 4,797,368 A | 1/1989 | Carter et al. |
| 5,602,034 A | 2/1997 | Tekamp-Olson |
| 5,691,176 A | 11/1997 | Lebkowski et al. |
| 5,693,531 A | 12/1997 | Chiorini et al. |
| 5,804,413 A | 9/1998 | DeLuca |
| 5,837,532 A | 11/1998 | Preston et al. |
| 5,846,782 A | 12/1998 | Wickham et al. |
| 5,849,571 A | 12/1998 | Glorioso et al. |
| 5,849,572 A | 12/1998 | Glorioso et al. |
| 5,858,355 A | 1/1999 | Glorioso et al. |
| 5,880,102 A | 3/1999 | George et al. |
| 5,885,958 A | 3/1999 | Zadina et al. |
| 5,998,174 A | 12/1999 | Glorioso et al. |
| 6,051,399 A | 4/2000 | Stout et al. |
| 6,087,129 A | 7/2000 | Newgard et al. |
| 6,156,304 A | 12/2000 | Glorioso et al. |
| 6,159,464 A | 12/2000 | Glorioso et al. |
| 6,210,393 B1 | 4/2001 | Brisken |
| 6,228,356 B1 | 5/2001 | Glorioso et al. |
| 6,268,213 B1 | 7/2001 | Samulski et al. |
| RE37,343 E | 8/2001 | Tekamp-Olson |
| 6,303,362 B1 | 10/2001 | Kay et al. |
| 6,303,578 B1 | 10/2001 | Zadina et al. |
| 6,337,319 B1 | 1/2002 | Wang |
| 6,413,511 B1 | 7/2002 | Glorioso et al. |
| 6,482,616 B1 | 11/2002 | Kovesdi et al. |
| 6,548,637 B1 | 4/2003 | Persons et al. |
| 6,596,269 B1 | 7/2003 | Iadarola et al. |
| 6,627,438 B2 | 9/2003 | Mehta et al. |
| 6,759,520 B1 | 7/2004 | Carr et al. |
| 6,770,449 B2 | 8/2004 | Barak et al. |
| 6,881,825 B1 | 4/2005 | Robbins et al. |
| 7,037,492 B2 | 5/2006 | Glorioso et al. |

(Continued)

FOREIGN PATENT DOCUMENTS

| | | |
|---|---|---|
| CN | 1958792 | 5/2007 |
| JP | 61-260885 | 11/1986 |
| WO | WO 91/02788 A1 | 3/1991 |
| WO | WO 96/04394 A1 | 2/1996 |
| WO | WO 98/15637 A1 | 4/1998 |

(Continued)

OTHER PUBLICATIONS

Krieger, T. et al., "Prohormone Thiol Protease and Enkephalin Precursor Processing: Cleavage at Dibasic and Monobasic Sites", 1992, J. Neurochemistry, vol. 59: pp. 26-31.*

(Continued)

*Primary Examiner*—Michael Burkhart
(74) *Attorney, Agent, or Firm*—Cohen & Grigsby, P.C.

(57) ABSTRACT

The invention provides an expression cassette comprising a DNA sequence encoding amino acids 1-99 of human preproenkephalin, a DNA sequence encoding a precursor of a carboxy-amidated peptide flanked by dibasic cleavage sites and optionally a DNA sequence encoding a marker protein (such as Enhanced Green Fluorescent Protein (GFP)) all in operable linkage and under control of a promoter. Where the encoded precursor of a carboxy-amidated peptide is an agonist for an opioid receptor, the invention further provides a method of treating neuropathic pain by administering the gene transfer vector comprising such an expression cassette to a patient. The invention also provides a method for detecting a peptide having a desired effect comprising introducing a library of DNA sequences encoding one or more precursors of carboxy-amidated peptides into host cells; expressing the carboxy-amidated peptides encoded in the library to provide expression products; and screening from the polypeptide expression products for the desired effect.

15 Claims, 10 Drawing Sheets

U.S. PATENT DOCUMENTS

| | | | |
|---|---|---|---|
| 7,045,344 | B2 | 5/2006 | Kay et al. |
| 7,176,298 | B2 | 2/2007 | Tchaga et al. |
| 7,304,036 | B2 | 12/2007 | Currie et al. |
| 2002/0090382 | A1 | 7/2002 | Glorioso et al. |
| 2002/0098168 | A1 | 7/2002 | Glorioso et al. |
| 2002/0164718 | A1 | 11/2002 | Tchaga et al. |
| 2003/0104622 | A1 | 6/2003 | Robbins et al. |
| 2003/0219826 | A1 | 11/2003 | Robbins et al. |
| 2003/0220283 | A1 | 11/2003 | Glorioso et al. |
| 2004/0043488 | A1 | 3/2004 | Glorioso et al. |
| 2005/0053922 | A1 | 3/2005 | Schaffer et al. |
| 2005/0074884 | A1 | 4/2005 | Robbins et al. |
| 2006/0105947 | A1 | 5/2006 | Carr et al. |
| 2006/0258593 | A1 | 11/2006 | Currie et al. |
| 2007/0060512 | A1 | 3/2007 | Sadeghi et al. |
| 2007/0224635 | A1 | 9/2007 | Bouquin |
| 2007/0259818 | A1 | 11/2007 | Skubatch |

FOREIGN PATENT DOCUMENTS

| | | |
|---|---|---|
| WO | WO 98/46722 A1 | 10/1998 |
| WO | WO 98/50563 A1 | 11/1998 |
| WO | WO 99/06583 A1 | 2/1999 |
| WO | WO 02/06316 A2 | 1/2002 |
| WO | WO 2006/132925 | 12/2006 |
| WO | WO 2007/112492 | 10/2007 |

OTHER PUBLICATIONS

Weber, E. et al., "Metorphamide: Isolation, structure, and biologic activity of an amidated opioid octapeptide from bovine brain", 1983, PNAS, vol. 80: pp. 7362-7366.*

"N-terminal acetylation and C-Terminal amidation of peptides", Thermo Scientific technical bulletin, 2 pages, printed Mar. 2009.*

Boddy, C., "Sweetening Cyclic peptide Libraries", 2004, Chem. and Biol.,vol. 11: pp. 1599-1600.*

Rosen, H. et al., "Isolation and Characterization of the Rat proenkephalin Gene", 1984, JBC, vol. 269: pp. 14309-14313.*

Foran et al., "A Substance P-Opioid Chimeric Peptide as a Unique Nontolerance-Forming Analgesic," *Proceedings of the National Academy of Sciences of USA*, 97(13): 7621-7626 (Jun. 20, 2000).

Mata et al., "Targeted Gene Delivery to the Nervous System Using Herpes Simplex Virus Vectors," *Physiology & Behavior*, 77(4-5): 483-488 (Dec. 2002).

Wolfe, D et al., Engineering an endomorphin-2 gene for use in neuropathic pain therapy, Pain, Dec. 15, 2007;133 (1-3): 29-38 Epub Mar. 28, 2007.

U.S. Appl. No. 11/445,835, filed Jun. 1, 2006, Wolfe et al.
U.S. Appl. No. 60/686,166, filed Jun. 1, 2005, Wolfe et al.
U.S. Appl. No. 60/686,845, filed Jun. 2, 2005, Wolfe et al.

Aicher et al., "Endomorphin-2 Axon Terminals Contact Mu-Opioid Receptor-Containing Dendrites in Trigeminal Dorsal Horn," *Brain Research*, 977: 190-198 (2003).

Ames et al., "BacMam Recombinant Baculoviruses in G Protein-Coupled Receptor Drug Discovery," *Receptors and Channels*, 10(3-4): 99-107 (2004).

Bailey et al., "Opioids: Cellular Mechanisms of Tolerance and Physical Dependence," *Current Opinion in Pharmacology*, 5(1): 60-68 (Feb. 2005).

Bednar et al." Kinetic Characterization of Novel NR2B Antagonists Using Fluorescence Detection of Calcium Flux," *Journal of Neuroscience Methods*, 137(2): 247-255 (2004).

Bennett et al., "A Peripheral Mononeuropathy in Rat That Produces Disorders of Pain Sensation Like Those Seen in Man," *Pain*, 33(1): 87-107 (1988).

Berkner, "Development of Adenovirus Vectors for the Expression of Heterologous Genes," *BioTechniques*, 6(7): 616-629 (Jul./Aug. 1988).

Bodo et al., "A Hot New Twist to Hair Biology Involvement of Vanillois Receptor-a (VR1/TRPV!) Signaling in Human Hair Growth Control," *American Journal of Pathology*, 166(4): 985-998 (Apr. 2005).

Bolkenius et al., "Peptidylglycine α-Amidating Mono-Oxygenase: Neuropeptide Amidation as a Target for Drug Design," *General Pharmacology*, 31(5): 655-659 (Nov. 1998).

Bras et al., "Herpes Simplex Virus 1-Mediated Transfer of Preproenkephalin A in Rat Dorsal Root Ganglia," *Journal of Neurochemistry*, 70(3): 1299-1303 (Mar. 1998).

Braz et al., "Therapeutic Efficacy in Experimental Polyarthritis of Viral-Driven Enkephalin Overproduction in Sensory Neurons," *The Journal of Neuroscience*, 21(20): 7881-7888 (Oct. 15, 2001).

Caterina et al., "The Capsaicin Receptor: A Heat-Activated Ion Channel in the Pain Pathway," *Nature*, 389(6653): 816-824 (Oct. 23, 1997).

Caterina et al., "Impaired Nociception and Pain Sensation in Mice Lacking the Capsaicin Receptor," *Science*, 288(5464): 306-313 (Apr. 14, 2000).

Chaplan et al., "Quantitative Assessment of Tactile Allodynia in the Rat Paw," *Journal of Neuroscience Methods*, 53(1): 55-63 (Jul. 1994).

Chen et al., "Endomorphin-1 and -2 Induce Naloxone-Precipitated Withdrawal Syndromes in Rats," *Peptides*, 24: 477-481 (2003).

Chen et al., "Herpes Simplex Virus Type 1 ICP0 Protein Does Not Accumulate in the Nucleus of Primary Neurons in Culture," *Journal of Virology*, 74(21): 10132-10141 (Nov. 2000).

Cheng et al., "Carvedilol and Vesmarinone: New Antiarrhythmic Approach in Heart Failure Therapy," *Acta Pharmacologica Sinica*, 22(3): 193-200 (Mar. 2001).

Chuang et al., "Gene Gun Particle Encoding Preproenkephalin cDNA Produces Analgesia Against Capsaicin-Induced Bladder Pain in Rats," *Urology*, 65(4): 804-810 (Apr. 2005).

Cortright et al., Biochemical Pharmacology of the Vanilloid Receptor TRPV1, *European Journal of Biochemistry*, 271(10): 1814-1819 (May 2004).

Cruz, "Mechanisms Involved in New Therapies for Overactive Bladder," *Urology*, 63(3A): 65-73 (Mar. 2004).

Dixon, "Efficient Analysis of Experimental Observations," *Annual Review of Pharmacology and Toxicology*, 20: 441-462 (1980).

Dutcher et al., "Phase II Study of Carboxyamidotriazole in Patients with Advanced Renal Cell Carcinoma Refractory to Immunotherapy," *Cancer*, 104(11): 2392-2399 (Dec. 1, 2005).

Egleton et al., "Development of Neuropeptide Drugs that Cross the Blood-Brain Barrier," *NeuroRx*, 2(1): 44-53 (Jan. 2005).

Eguchi, "Recent Advances in Selective Opioid Receptor Agonists and Antagonists," *Medicinal Research Reviews*, 24(2): 182-212 (Mar. 2004).

Eipper et al., "The Biosynthesis of Neuropeptides: Peptide α-Amidation," *Annual Review of Neuroscience*, 15: 57-85 (1992).

El Kouchen et al., "A-425619 [1-lsoquinolin-5-yl-3-(4-Trifluoromethyl-Benzyl)-urea], A Novel and Selective Transient Receptor Potential Type V1 Receptor Antagonist, Blocks Channel Activation by Vanilloids, Heat and Acid," *The Journal of Pharmacology and Experimental Therapeutics*, 314(1): 400-409 (2005).

Fichna et al., "Characterization of Antinociceptive Activity of Novel Endomorphin-2 and Morphiceptin Analogs Modified in the Third Position," *Biochemical Pharmacology*, 69: 179-185 (2005).

Finking et al., "Biosynthesis of Nonribosomal Peptides," *Annual Review of Microbiology*, 58: 453-488 (2004).

Girard et al., "Molecular Cloning and Functional Analysis of SUT-1, A Sulfate Transporter From Human High Endothelial Venules," *Proceeding of the National Academy of Sciences of the United States of America*, 96(22): 12772-12777 (Oct. 26, 1999).

Glorioso et al., "Herpes Vector-Mediated Gene Transfer in Treatment of Diseases of the Nervous System," *Annual Review of Microbiology*, 58: 253-271 (2004).

Goins et al., "Development of Replication-Defective Herpes Simplex Virus Vectors," *Gene Therapy Protocols*, (Morgan, ed), 481-507 (Humana Press, Totowa, NJ, 2002).

Gold, "Spinal Nerve Ligation: What to Blame For the Pain and Why," *Pain*, 84(2-3): 117-120 (Feb. 2000).

Goss et al., "Antinociceptive Effect of a Genomic Herpes Simplex Virus-based Vector Expressing Human Proenkephalin in Rat Dorsal Root Ganglion," *Gene Therapy*, 8(7): 551-556 (Apr. 2001).

Goss et al., "Herpes Vector-Mediated Expression of Proenkephalin Reduces Bone Cancer Pain," *Annals of Neurology*, 52(5): 662-665 (Nov. 2002).

Goss et al., "Delivery of Herpes Simplex Virsus-Based Vectors to the Nervous System," *Methods in Molecular Biology*, 246: 309-322 (2004).

Grant et al., "Delay of Intracellular Calcium Transients Using a Calcium Chelator: Application to High-Throughput Screening of the Capsaicin Receptor Ion Channel and G-Protein-Coupled Receptors," *Analytical Biochemistry*, 294(1): 27-35 (Jul. 1, 2001).

Gu et al., "Remote Nerve Injection of Mu Opioid Receptor Adeno-Associated Viral Vector Increases Antinociception of Intrathecal Morphine," *The Journal of Pain*, 6(7): 447-454 (Jul. 2005).

Gunthorpe et al., "Identification and Characterisation of SB-366791, A Potent and Selctive Vanilloid Receptor (VR1/TRPV1) Antagonist," *Neuropharmacology*, 46(1): 133-149 (Jan. 2004).

Hamman et al., "Oral Delivery of Peptide Drugs," *Biodrugs*, 19(3): 165-177 (2005).

Hao et al., "Transgene-Mediated Enkephalin Release Enhances the Effect of Morphine and Evades Tolerance to Produce a Sustained Antiallodynic Effect in Neuropathic Pain," *Pain*, 102(1-2): 135-142 (Mar. 2003).

Hao et al., "Gene Transfer of Glutamic Acid Decarboxylase Reduces Neuropathic Pain," *Annals of Neurology*, 57(6): 914-918 (Jun. 2005).

Hargreaves et al., "A New and Sensitive Method for Measuring Thermal Nociception in Cutaneous Hyperalgesia," *Pain*, 32(1): 77-88 (Jan. 1988).

Hirata et al., "A Model of Peripheral Mononeuropathy in the Rat," *Pain*, 42(2): 253-255 (Aug. 1990).

Hobbs et al., "Perturbation of Cell Cycle Progression and Cellular Gene Expression as a Function of Herpes Simplex Virus ICP0," *Journal of Virology*, 73(10): 8245-8255 (Oct. 1999).

Hofmann et al., "A Database of Membrane Spanning Protein Segments," *Biological Chemistry Hoppe-Seyler*, 374(3): 166 (Mar. 1993).

Hong et al., "Early Painful Diabetic Neuropathy Is Associated With Differential Changes in the Expression and Function of Vanilloid Receptor," *The Journal of Biological Chemistry*, 280(1): 618-627 (Jan. 7, 2005).

Hook et al., "Cathepsin L and Arg/Lys Aminopeptidase: A Distinct Prohormone Processing Pathway for the Biosynthesis of Peptide Neurotransmitters and Hormones," *Biological Chemistry*, 385(6): 473-480 (Jun. 2004).

Hübner et al., "Ion Channel Diseases," *Human Molecular Genetics*, 11(20): 2435-2445 (2002).

Jaffe et al., "Adenoviral Mediated Transfer and Expression of a Normal Human α1-Antitrypsin cDNA in Primary Rat Hepatocytes," *Clinical Reasearch*, 39(2): 302A (Apr. 1991).

Jäger et al. "New Fluorescence Techniques for High-Throughput Drug Discovery," *Current Pharmaceutical Biotechnology*, 4(6): 463-476 (2003).

Jambrina et al., "Calcium Influx Through Receptor-Operated Channel Induces Mitochondria-Triggered Paraptotic Cell Death," *The Journal of Biological Chemistry*, 278(16): 14134-14145 (Apr. 18, 2003).

Janecka et al., "Synthesis and Antinociceptive Activity of Cyclic Endomorphin-2 and Morphiceptin Analogs," *Biochemical Pharmacology*, 71: 188-195 (2005).

Janecka et al., "Enzymatic Degradation Studies of Endomorphin-2 and its Analogs Containing N-Methylated Amino Acids," *Peptides*, 27(1): 131-135 (Jan. 2006).

Julius, "Another Opiate for the Masses?" *Nature*, 386(6624): 442 (Apr. 3, 1997).

Kalso, "Sodium Channel Blockers in Neuropathic Pain," *Current Pharmaceutical Design*, 11(23): 3005-3011 (2005).

Kastin et al., "Saturable Brain-To-Blood Transport of Endomorphins," *Experimental Brain Reasearch*, 139(1): 70-75 (Jul. 2001).

Kim et al., "An Experimental Model for Peripheral Neuropathy Produced by Segmental Spinal Nerve Ligation in the Rat," *Pain*, 50(3): 355-363 (Sep. 1992).

Krisky et al., "Development of Herpes Simplex Virus Replication-Defective Multigene Vectors for Combination Gene Therapy Applications," *Gene Therapy*, 5: 1517-1530 (1998).

Krisky et al., "Deletion of Multiple Immediate-Early Genes From Herpes Simplex Virus Reduces Cytotoxicity and Permits Long-Term Gene Expression in Neurons," *Gene Therapy*, 1593-1603 (1998).

Lipton, "Failures and Successes of NMDA Receptor Antagonist: Molecular Basis for the Use of Open-Channel Blockers Like Memantine in the Treatment of Acute and Chronic Neurologic Insults," *NeuroRx*, 1(1): 101-110 (Jan. 2004).

Liu et al., "Initial Processing of Human Proenkephalin in Bovine Chromaffin Cells," *Journal of Neurochemistry*, 67(4): 1457-1462 (Oct. 1996).

Liu et al., "Peripherally Delivered Glutamic Acid Decarboxylase Gene Therapy for Spinal Cord Injury Pain," *Molecular Therapy*, 10(1): 57-66 (Jul. 2004).

Lledo, "Exocytosis in Excitable Cells: A Conserved Molecular Machinery From Yeast to Neuron," *European Journal of Endocrinology*, 137(1): 1-9 (Jul. 1997).

Loh et al., "Mechanism of Sorting Proopiomelanocortin and Proenkephalin to the Regulated Secretory Pathway of Neuroendocrine Cells," *Annals of The New York Academy of Sciences*, 971: 416-425 (2002).

Marconi et al., "Replication-Defective Herpes Simplex Virus Vectors for Gene Transfer In Vivo," *Proc. Natl. Acad. Sci. USA*, 93(21): 11319-11320 (Oct. 15, 1996).

Mayer et al., "Cellular Mechanisms of Neuropathic Pain, Morphine Tolerance, and Their Interactions," *Proceedings of the National Academy of Sciences of the United States of America*, 96(14): 7731-7736 (Jul. 6, 1999).

McGaraughty et al., "Systemic and Site-Specific Effects of A-425619, a Selective TRPV1 Receptor Antagonist, on Wide Dynamic Range Neurons in CFA-Treated and Uninjured Rats," *J Neurophysiol*, 95(1): 18-25 (Jan. 2006).

McNicol et al., "Management of Opioid Side Effects in Cancer-Related and Chronic Noncancer Pain: A Systematic Review," *The Journal of Pain*, 4(5): 231-256 (Jun. 2003).

Meunier et al., "Attenuation of Pain-Related Behavior in a Rat Model of Trigeminal Neuropathic Pain by Viral-Driven Enkephalin Overproduction in Trigeminal Ganglion Neurons," *Molecular Therapy*, 11(4): 608-616 (Apr. 2005).

Miljanich, "Ziconotide: Neuronal Calcium Channel Blocker for Treating Severe Chronic Pain," *Current Medicinal Chemistry*, 11(23): 3029-3040 (Dec. 2004).

Milligan et al. "Controlling Neuropathic Pain by Adeno-Associated Virus Driven Production of the Anti-Inflammatory Cytokine, Interleukin-10," *Molecular Pain*, 1(9): 1-13 (2005).

Milligan et al., "Controlling Pathological Pain by Adenovirally Driven Spinal Production of the Anti-Inflammatory Cytokine, Interleukin-10," *European Journal of Neuroscience*, 21(8): 2136-2148 (Apr. 2005).

Mizoguchi et al., "Loss of μ-Opioid Receptor-Mediated G-Protein Activation in the Pons/Medulla of Mice Lacking the Exons 2 and 3 of μ-Opioid Receptor Gene," *Neuroscience Letters*, 335(2): 91-94 (Dec. 25, 2002).

Mizoguchi et al., "Lacking of μ-Opioid Receptor-Mediated G-Protein Activation in the Spinal Cord of Mice Lacking Exon 1 or Exons 2 and 3 of the MOR-1 Gene," *Journal of Pharmacological Sciences*, 93(4): 423-429 (Dec. 2003).

NCBI, "Homo sapiens proenkephalin (PENK), mRNA," Database Entre-Nucleotice, Accession No. NM_006211 (Oct. 14, 2005). Retrieved Jun. 20, 2006.

NCBI, "tachykinin 1 isoform beta precursor (Homo sapiens)," Database Entre-Protein, Accession No. NP_003173 (Apr. 16, 2006). Retrieved Jun. 20, 2006.

NCBI, "Corticotropin-lipotropin precursor (Pro-opiomelanocortin) (POMC) [Contains: NPP; Melanotropin gamma (Gamma-MSH); Potential peptide; Corticotropin (Adrenocorticotropic hormone) (ACTH); Melanotropin alpha (Alpha-MSH); Corticotropin-like intermediary peptide (CLIP); Lipotropin beta (Beta-LPH); Lipotropin gamma (Gamma-LPH); Melanotropin beta (Beta-MSH); Beta-endorphin; Met-enkephalin]," Database Entre-Protein, Accession No. P01189 (Jun. 13, 2006). Retrieved Jun. 20, 2006.

NCBI, FMRFamide-related peptides precursor [Contains: Neuropeptide NPSF (Neuropeptide RFRP-1); Neuropeptide RFRP-2; Neuropeptide NPVF (neuropeptide RFRP-30], Database Entre-Protein, Accession No. Q9HCQ7 (Apr. 18, 2006) Retrieved Jun. 20, 2006).

Nikam et al., "AMPA Receptor Antagonists," *Current Medicinal Chemistry*, 8(2): 155-170 (2001).

Niranjan et al., "Treatment of Rat Gliosarcoma Brain Tumors by HSV-Based Multigene Therapy Combined with Radiosurgery," *Molecular Therapy*, 8(4): 530-542 (Oct. 2003).

Nydahl et al., "Co-Localization of Endomorphin-2 and Substance P in Primary Afferent Nociceptors and Effects of Injury: A Light and Electron Microscopic Study in the Rat," *European Journal of Neuroscience*, 19(7): 1789-1799 (Apr. 2004).

Obara et al., "Local Peripheral Effects of μ-Opioid Receptor Agonists in Neuropathic Pain in Rats," *Neuroscience Letters*, 360(1-2): 85-89 (Apr. 22, 2004).

Okada et al., "Endomorphins and Related Opioid Peptides," *Vitamins and Hormones*, 65: 257-279 (2002).

Ouafik et al., "The Multifunctional Peptidylglycine α-Amidating Monooxygenase Gene: Exon/Intron Organization of Catalytic, Processing , and Routing Domains," *Molecular Endocrinology*, 6(10): 1571-1584 (Oct. 1992).

Owen et al., "A New Proposal for the Mechanism of Glycine Hydroxylation as Catalyzed by Peptidylglycine α-Hydroxylating Monooxygenase (PHM)," *Medical Hypotheses*, 62(3): 392-400 (2004).

Primeaux et al., "Herpes Virus-Mediated Preproenkephalin Gene Transfer in the Ventral Striatum Mimics Behavioral Changes Produced by Olfactory Bulbectomy in Rats," *Brain Research*, 988(1,2): 43-55 (Oct. 24, 2003).

Przewlocki et al., "Opioids in Neuropathic Pain," *Current Pharmaceutical Design*, 11(23): 3013-3025 (2005).

Puskovic et al., "Prolonged Biologically Active Transgene Expression Driven by HSV LAP2 in Brain in Vivo," *Molecular Therapy*, 10(1): 67-75 (Jul. 2004).

Ramsey et al., "An Introduction to TRP Channels," *Annual Review of Physiology*, 68: 619-647 (2006).

REIS et al., "Levetiracetam Influences Human Motor Cortex Excitability Mainly by Modulation of Ion Channel Function—A TMS Study," *Epilepsy Research*, 62(1): 41-51 (Nov. 2004).

Rónai et al., "Endomorphin Synthesis in Rat Brain From Intracerebroventricularly Injected [$^3$H]-Tyr-Pro: A Possible Biosynthetic Route for Endomorphins," *Regulatory Peptides*, 134(1): 54-60 (Mar. 15, 2006).

Rosenfeld et al., "Adenovirus-Mediated Transfer of a Recombinant α1-Antitrypsin Gene to the Lung Epithelium in Vivo," *Science*, 252(5004): 431-434 (Apr. 19, 1991).

Rosenfeld et al., "In Vivo Transfer of the Human Cystic Fibrosis Gene to the Respiratory Epithelium," *Clinical Research*, 39(2): 311A (Apr. 1991).

Samaniego et al., "Persistence and Expression of the Herpes Simplex Virus Genome in the Absence of Immediate-Early Proteins," *Journal of Virology*, 72(4): 3307-3320 (Apr. 1998).

Sculptoreanu et al., "Protein Kinase C Is Involved in Neurokinin Receptor Modulation of N- and L-Type $Ca^{2+}$ Channels in DRG Neurons of the Adult Rat," *Journal of Neurophysiology*, 90(1): 21-31 (Jul. 2003).

Sculptoreanu et al., "Protein Kinase C Contributes to Abnormal Capsaicin Responses in DRG Neurons From Cats With Feline Interstitial Cystitis," *Neuroscience Letters*, 381(1-2): 42-46 (Jun. 2005).

Seltzer et al., "A Novel Behavioral Model of Neuropathic Pain Disorders Produced in Rats by Partial Sciatic Nerve Injury," *Pain*, 43(2): 205-218 (Nov. 1990).

Shin et al., "Essential Role of Mitochondrial Permeability Transition in Vanilloid Receptor 1-Dependent Cell Death of Sensory Neurons," *Molecular and Cellular Neuroscience*, 24(1): 57-68 (Sep. 2003).

Smart et al., "The Endogenous Lipid Anandamide is a Full Agonist at the Human Vanilloid Receptor (hVR1)," *British Journal of Pharmacology*, 129(2): 227-230 (Jan. 2000).

Smith et al., "Decreases in Endomorphin-2-Like Immunoreactivity Concomitant With Chronic Pain After Nerve Injury," *Neuroscience*, 105(3): 773-778 (2001).

Sneddon et al., "Obligate Mitogen-Activated Protein Kinase Activation in Parathyroid Hormone Stimulation of Calcium Transport But Not Calcium Signaling," *Endocrinology*, 141(11): 4185-4193 (Nov. 2000).

Soignier et al., "Analgesic Effects of Endomorphin-1 and Endomorphins-2 in the Formalin Test in Mice," *Life Sciences*, 67: 907-912 (2000).

Soignier et al., "Analgesic Tolerance and Cross-Tolerance to i.c.v. Endomorphin-1, Endomorphin-2, and Morphine in Mice," *Neuroscience Letters*, 366(2): 211-214 (Aug. 12, 2004).

Sora et al., "Opiate Receptor Knockout Mice Define μ Receptor Roles in Endogenous Nociceptive Responses and Morphine-Induced Analgesia," *Proceedings of the National Academy of Sciences of the United States of America*, 94(4): 1544-1549 (Feb. 18, 1997).

Stavrovskaya et al., "The Powerhouse Takes Control of the Cell: Is the Mitochondrial Permeability Transition a Viable Therapeutic Target Against Neuronal Dysfunction and Death," *Free Radical Biology & Medicine*, 38(6): 687-697 (Mar. 15, 2005).

Szabó et al., "Role of Transient Receptor Potential Vanilloid 1 Receptors in Adjuvant-Induced Chronic Arthritis: In Vivo Study Using Gene-Deficient Mice," *The Journal of Pharmacology and Experimental Therapeutics*, 314(1): 111-119 (2005).

Tominaga et al., "The Cloned Capsaicin Receptor Integrates Multiple Pain-Producing Stimuli," *Neuron*, 21(3): 531-543 (Sep. 1998).

Tseng, "The Antinociceptive Properties of Endomorphin-1 and Endomorphin-2 in the Mouse," *The Japanese Journal of Pharmacology*, 89(3): 216-220 (Jul. 2002).

Turk et al., "Peptide Libraries: At the Crossroads of Proteomics and Bioinformatics," *Current Opinion in Chemical Biology*, 7(1):84-90 (Feb. 2003).

Ueda, "Locus-Specific Involvement of Anti-Opioid Systems in Morphine Tolerance and Dependence," *Annals of the New York Academy of Science*, 1025: 376-382 (2004).

Varga et al., Effects of the Novel TRPV1 Receptor Antagonist SB366791 in Vitro and in Vivo in the Rat, *Neuroscience Letters*, 385(2): 137-142 (Sep. 9, 2005).

Von Eggelkraut-Gottanka et al., "Biosynthesis of Peptide Hormones Derived from Precursor Sequences," *Current Medicinal Chemistry*, 11(20): 2651-2665 (Oct. 2004).

Wang et al., "Recent Advances in the Search for the μ-Opioidergic System Morphological Studies of the Endomorphinergic Neurons in the Central Nervous System," *The Japanese Journal of Pharmacology*, 89(3): 209-215 (Jul. 2002).

Wolfe et al., "Design and Use of Herpes Simplex Viral Vectors for Gene Therapy," *Gene Therapy Therapeutic Mechanisms and Strategies*, (Templeton et al., eds) 81-108 (Marcel Dekker, Inc. New York, 2000).

Wu et al., "Regulated, Electroporation-Mediated Delivery of Pro-Opiomelanocortin Gene Suppresses Chronic Constriction Injury-Induced Neuropathic Pain in Rats," *Gene Therapy*, 11(7): 933-940 (Apr. 2004).

Xu et al., "Adeno-Associated Viral Transfer of Opioid Receptor Gene to Primary Sensory Neurons: A Strategy to Increase Opioid Antinociception," *Proceedings of the National Academy of Sciences of the United States of America*, 100(10): 6204-6209 (May 13, 2003).

Ye et al., "Ondansetron: A Selective 5-$HT_3$ Receptor Antagonist and Its Applications in CNS-Related Disorders," *CNS Drug Reviews*, 7(2): 199-213 (Summer 2001).

Yeomans et al., "Recombinant Herpes Vector-Mediated Analgesia in a Primate Model of Hyperalgesia," *Molecular Therapy*, 13(3): 589-597 (Mar. 2006).

Zadina et al., "A Potent and Selective Endogenous Agonist for the µ-Opiate Receptor," *Nature*, 386(6624): 499-502 (Apr. 3, 1997).

Zadina, "Recent Advances in the Search for the µ-Opioidergic System; Isolation and Distribution of Endomorphins in the Central Nervous System," *The Japanese Journal of Pharmacology*, 89(3): 203-208 (Jul. 2002).

Zheng et al., "Vanilloid Receptors in Hearing: Altered Cochlear Sensitivity by Vanilloids and Expression of TRPV1 in the Organ of Corti," *Journal of Neurophysiology*, 90(1): 444-455 (Jul. 2003).

Zheng et al., "High Throughput Assay Technologies for Ion Channel Drug Discovery," *Assay and Drug Development Technologies*, 2(5): 543-552 (2004).

\* cited by examiner

METHOD OF AMIDATED PEPTIDE BIOSYNTHESIS AND DELIVERY IN VIVO: ENDOMORPHIN-2 FOR PAIN THERAPY

CROSS-REFERENCE TO RELATED APPLICATIONS

This patent application claims the benefit of U.S. Provisional Patent Application No. 60/686,253, filed Jun. 1, 2005, which is incorporated herein by reference.

STATEMENT REGARDING FEDERALLY SPONSORED RESEARCH AND DEVELOPMENT

This invention was made in part with Government support under Grant Number NS044507 awarded by the National Institutes of Health. The Government may have certain rights in this invention.

BACKGROUND OF THE INVENTION

The mu opioid receptor is a G protein coupled receptor expressed in the central and peripheral nervous system, and is activated by opioid compounds such as morphine. Such opioids have been used for centuries to provide effective pain relief and continue to be essential tools in modern clinical pain management. However, the clinical utility of opioid drugs is limited by side effects including gastrointestinal complications, respiratory depression. The clinical utility of opioid drugs is further limited by the possibility that patients will develop tolerance or dependency over long-term use. Endogenous opioids, such as the carboxy-amidated tetrapeptide, endomorphin-2 (EM-2), binds the mu opioid receptor with high affinity and are analgesic in several animal models of pain. However, while endomorphin peptides have been isolated from bovine and human brain, no gene sequences corresponding to a potential preproendomorphin gene have been identified in human genome sequence databases, which renders the production and use of endomorphins problematic. Accordingly, there is a need for a genetic expression system for expressing carboxy-aminated peptides, such as endomorphins.

BRIEF SUMMARY OF THE INVENTION

The invention provides an expression cassette comprising a first DNA sequence selected from the group consisting of a DNA sequence encoding amino acids 1-99 of human preproenkephalin, a DNA sequence encoding amino acids 1-58 of tachykinin 1 isoform beta precursor, a DNA sequence encoding amino acids 1-26 of corticotrophin-lipotropin precursor, and a DNA sequence encoding amino acids 1-55 of FMRFamide-related peptide precursor; a second DNA sequence encoding a precursor of a peptide flanked by cleavage sites; and optionally a DNA sequence encoding a marker protein (such as Green Fluorescent Protein (GFP)) all in operable linkage and under control of a promoter.

Where the encoded precursor of a peptide is a carboxy-amidated peptide that is an agonist for an opioid receptor, the invention further provides a method of treating neuropathic pain by administering the gene transfer vector comprising such an expression cassette to a patient.

The invention also provides a method for detecting a peptide having a desired effect comprising introducing a library of DNA sequences encoding one or more precursors of peptides into host cells; expressing the peptides encoded in the library to provide expression products; and screening from the polypeptide expression products for the desired effect.

These advantages, and additional inventive features, will be apparent from the following description of the invention and the accompanying drawings.

DETAILED DESCRIPTION OF THE INVENTION

Figure 1:
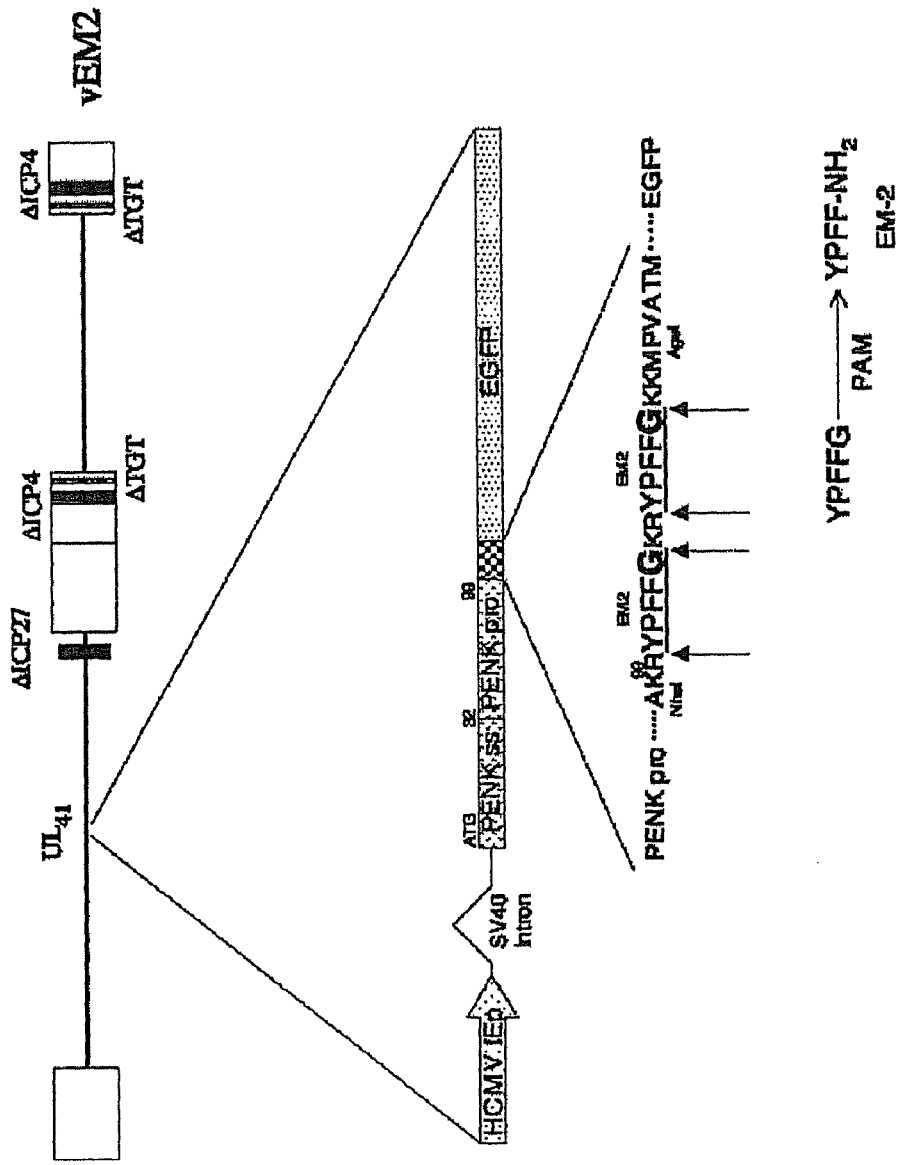
FIG. 1. Schematic representation of the EM-2 expression vector construction. An HCMV IEp:EM-2 expression cassette was introduced into the UL41 locus of the replication defective HSV (QOZ) genome. Arrows indicate dibasic cleavage sites. The EM-2 prepeptide is underlined including the glycine reside extension in bold (G). After cleavage, the liberated EM-2 propeptide (YPFFG) is designed to be processed by PAM into EM-2 proper (YPFF-NH2).

The invention relates to preparation and uses of a synthetic expression cassette to direct production, cleavage, and processing of peptides, such as EM2. The expression cassette comprises (a) a DNA sequence encoding a signal sequence of a preproprotein; (b) a DNA sequence encoding a precursor of a peptide flanked by cleavage sites; and optionally (b) a DNA sequence encoding a signal peptide (such as Green Fluorescent Protein (GFP) or luciferase). These elements are in operable linkage such that all are transcribed in frame within the expression cassette. The expression cassette can be constructed using ordinary molecular cloning techniques, which are well known to those of ordinary skill in the art. The separate elements of the expression cassette can be cloned (e.g., using PCR) or synthesized and ligated together to construct the cassette. If desired, the sequence of the construct can be confirmed by standard sequencing techniques.

The signal sequence can be drawn from a protein such as human preproenkephalin (PPE) (Accession No. NM_006211), tachykinin 1 isoform beta precursor (Accession No. NP_003173), corticotrophin-lipotropin precursor (Accession No. P01189), or FMRFamide-related peptide precursor (Accession No. Q9HCQ7). The signal sequence of a preproprotein is located in the amino-terminal domain of the protein. In preferred embodiments, the expression cassette includes a DNA sequence encoding amino acids 1-99 of human PPE (SEQ ID NO: 1). In other embodiments, the expression cassette can comprise a DNA sequence encoding a signal sequence of another protein such as amino acids 1-58 of tachykinin 1 isoform beta precursor (SEQ ID NO:2), amino acids 1-26 of corticotrophin-lipotropin precursor (SEQ ID NO:3), or amino acids 1-55 of FMRFamide-related peptide precursor (SEQ ID NO:4). Without wishing to be bound by theory, each of these preproprotein signal sequences is believed to contain residues that direct polypeptides into the regulated secretory pathway where proteolytic processing occurs (see references 13, 14, and 37).

Within the expression cassette, the preproprotein signal sequence can be followed in frame by a second DNA sequence encoding one or more precursors of a peptide, flanked by cleavage sites. In preferred embodiments, the peptide can be a carboxy-amidated peptide. In other embodiments, the peptide can be a cyclic peptide or another type of peptide. The cleavage sites are preferably dibasic cleavage sites, however, the cleavage sites can also be furin cleavage sites, or carboxypeptidase cleavage sites. In some embodiments, the expression cassette comprises two or more DNA sequences encoding precursors of carboxy-amidated peptides, wherein each DNA sequence encoding a precursor of a carboxy-amidated peptide is flanked by dibasic cleavage sites.

The precursor of a peptide can comprise between two and about twenty amino acids. Preferably, the precursor comprises between four and 18 amino acids. Thus, the precursor can comprise 2, 3, 4, 5, 6, 7, 8, 9, 10, 11, 12, 13, 14, 15, 16, 17, 18, 19, or 20 amino acids. In embodiments wherein the peptide is a carboxy-amidated peptide, the precursor encoded in the expression cassette can have a carboxyl extended glycine residue.

In a preferred embodiment, the carboxy-amidated peptide can be an agonist of an opioid receptor. Preferably, the carboxy-amidated peptide is an agonist of the mu opioid receptor. Carboxy-amidated peptides of the present invention can also be agonists of the delta opioid receptor. In preferred embodiments, the carboxy-amidated peptide is Endomorphin-1 having a peptide sequence YPWF (SEQ ID NO:5) or Endomorphin-2, having a peptide sequence YPFF (SEQ ID NO:6). Accordingly, the peptide sequence of the precursor of Endomorphin-1 can be YPWFG (SEQ ID NO:7), and similarly, the peptide sequence of the precursor of Endomorphin-2 can be YPFFG (SEQ ID NO:8). In some preferred embodiments, the one or more precursors can be a pair of Endomorphin-2 coding elements each flanked by dibasic cleavage sites.

Without being bound by theory, it is thought that preproprotein signal sequences such as PPE mimic the biosynthesis of prototypical secretory peptides from genome-encoded preproproteins. In turn, peptides are produced as protein precursors that undergo posttranslational processing to yield the functional peptide. The dibasic residues flanking the core peptide sequence are recognized by proteases and/or aminopeptidases whose proteolytic activity liberates the peptide from the protein precursor (see references 15 and 16). In some preferred embodiments such as the production of endomorphins, following peptide liberation, carboxy-terminal glycine residues are processed in the endoplasmic reticulum by the bifunctional enzyme peptidylglycine a-amidating monooxygenase (PAM; EC 1.14.17.3) to yield a free carboxy-amidated peptide within the RSP (see references 17-19) of the trans-golgi network.

Within the expression cassette, the DNA sequence encoding one or more precursors of a peptide flanked by cleavage sites preferably is fused in frame with the open reading frame of a marker protein, advantageously allowing efficient cleavage and providing a biomarker. A desired biomarker protein is GFP, however, other markers (typically fluorescent) can be used instead. It will be understood that, while the DNA sequence encoding one or more precursors of a peptide, flanked by cleavage sites is fused in frame with the preproprotein signal sequence and optionally the marker protein, intervening sequences (such as IRES) can be included as well.

While the invention provides the expression cassette in isolated form, the invention also pertains to a population comprising a plurality of the expression cassettes. Typically, the population includes thousands of such cassettes. The population can be generated by amplification (e.g., using PCR) of a single cassette or by introducing the cassette into a cloning vector (e.g., a plasmid or phage) and amplifying the vector in a suitable host system such as bacteria). It will be observed that the population can be clonal, in which instance, it is substantially homologous (accounting for occasional errors during replication) and most desirably homologous.

In other embodiments, the population defines a random or semirandom library, in which the DNAs encoding the precursors of peptides differ. Typically, such a library will contain scores of different sequences. More preferably hundreds (at least 100) or even thousands (at least 1000 or at least 10,000) of different expression cassettes differing in the sequence of DNAs encoding the precursors of peptides, such as carboxy-amidated peptides, cyclic peptides, and/or other types of peptides, constitute the library. Such a library can be constructed by first generating a population of random or semirandom oligonucleotides encoding precursors of peptides having one or more desired characteristics (e.g., precursors of carboxy-amidated peptides, encoding a carboxy-terminal glycine residues). This population of oligonucleotides then can be cloned into the cassette backbone—i.e., in frame with the prepropro-tein signal sequence and optional biomarker.

A preferred method for constructing such random or semi-random libraries employs the GATEWAY® system (Invitrogen, Carlsbad, Calif.). In the GATEWAY® system, ccdB is used as a negative selectable marker that if present kills the bacteria cell. ccdB is replaced by a random or semirandom sequence through site specific recombination carried out by a modified lambda integrase. Two relevant bacterial strains are used in GATEWAY® technology, ccdB sensitive and ccdB resistant. The ccdB containing plasmid is propagated in ccdB resistant bacteria and purified. This plasmid is then used for in vitro recombination. The recombination product is transformed into a ccdB sensitive bacteria selecting for plasmids that have had the ccdB gene replaced by the gene-of-interest during the in vitro recombination. By replacing ccdB, the background in cloning and library construction is dramatically reduced or eliminated allowing the shuttling of genes into and out or a variety of plasmids at will. As a starting point the base plasmids must be grown in bacteria that are resistant to the toxic effects of ccdB of which there are a very limited number of genotypes available. Invitrogen markets a single ccdB resistant bacterial strain, but this strain does not accommodate large vectors (such as bacterial artificial chromosomes ("BACs")) needed to accommodate larger viral vectors, such as HSV. Accordingly, to employ the GATEWAY® technology in the context of the invention using a large viral vector system, a bacterial strain amenable to transformation to large DNAs (such as BACs) desirably is modified to express a gene that confers insensitivity to ccdB. A preferred strain is derived from the DH10B bacterial strain used in BAC propagation and manipulation, which also has a mutation (fhuA::IS2) that increases their proclivity to transformation by very large DNAs.

The expression cassette (or library) can be placed into an expression vector system under control of a suitable promoter. A desired promoter is a constitutively active promoter, such as a human cytomegalovirus (hCMV) immediate-early promoter, although other promoters known to those of skill in the art can be employed. Alternatively, in some embodiments, an inducible promoter or temperature-sensitive promoter can be employed, such as a tetracycline-regulated inducible promoter. Other promoters that can be used in embodiments of the present invention include ubiquitin promoters, such as a ubiquitin C promoter (Invitrogen, Carlsbad, Calif.); a human elongation factor-1É (EF-1É) promoter available from Invitrogen (Carlsbad, Calif.); a Rous Sarcoma Virus (RSV) promoter, as described, for example, in Yamamoto, et al., Cell 22(3):787-97 (1980); an HSV ICP0 promoter; and an HSV LAP2 promoter, described in U.S. Pat. No. 5,849,571. Techniques for introducing genetic constructs, such as the inventive expression cassette, into expression vector systems are known, and any suitable technique (such as homologous recombination) can be employed.

In a preferred embodiment, the vector system is an HSV based viral vector system suitable for use as a vector to introduce a nucleic acid sequence into numerous cell types. The mature HSV virion consists of an enveloped icosahedral capsid with a viral genome consisting of a linear double-stranded DNA molecule that is 152 kb. In a preferred embodiment, the HSV based viral vector is deficient in at least one essential HSV gene. Of course, the vector can alternatively or in addition be deleted for non-essential genes. Preferably, the HSV based viral vector that is deficient in at least one essential HSV gene is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP 4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, 5,849, 572, and 5,804,413, and International Patent Applications WO 91/02788, WO 96/04394, WO 98/15637, and WO 99/06583, which are incorporated herein by reference. Preferably, the HSV vector is "multiply deficient," meaning that the HSV vector is deficient in more than one gene function required for viral replication. The sequence of HSV is available on the internet at www.ncbi.nlm.nih.gov:80/entrez/query.fcgi?cmd=Retrieve&db=nucleotide&list_uids=9629378&dopt=GenBank&term=hsv-1&qty=1, which may facilitate the generation of desired mutations in designing vectors.

The HSV vector can be deficient in replication-essential gene functions of the early regions of the HSV genome, the immediate-early regions of the HSV genome, only the late regions of the HSV genome, or both the early and late regions of the HSV genome. The HSV vector also can have essentially the entire HSV genome removed, in which case it is preferred that at least either the viral inverted terminal repeats (ITRs) and one or more promoters or the viral ITRs and a packaging signal are left intact (i.e., an HSV amplicon). The larger the region of the HSV genome that is removed, the larger the piece of exogenous nucleic acid sequence that can be inserted into the genome. However, it is preferred that the vector of the present invention be a non-amplicon HSV vector.

It should be appreciated that the deletion of different regions of the HSV vector can alter the immune response of the mammal. In particular, the deletion of different regions can reduce the inflammatory response generated by the HSV vector. Furthermore, the HSV vector's protein coat can be modified so as to decrease the HSV vector's ability or inability to be recognized by a neutralizing antibody directed against the wild-type protein coat.

The HSV vector, when multiply replication deficient, preferably includes a spacer element to provide viral growth in a complementing cell line similar to that achieved by singly replication deficient HSV vectors. The spacer element can contain any nucleic acid sequence or sequences which are of the desired length. The spacer element sequence can be coding or non-coding and native or non-native with respect to the HSV genome, but does not restore the replication essential function(s) to the deficient region. In addition, the inclusion of a spacer element in any or all of the deficient HSV regions will decrease the capacity of the HSV vector for large inserts. The production of HSV vectors involves using standard molecular biological techniques well known in the art.

Replication deficient HSV vectors are typically produced in complementing cell lines that provide gene functions not present in the replication deficient HSV vectors, but required for viral propagation, at appropriate levels in order to generate high titers of viral vector stock. A preferred cell line complements for at least one and preferably all replication essential gene functions not present in a replication deficient HSV vector. The cell line also can complement non-essential genes that, when missing, reduce growth or replication efficiency (e.g., UL55). The complementing cell line can complement for a deficiency in at least one replication essential gene function encoded by the early regions, immediate-early regions, late regions, viral packaging regions, virus-associated regions, or combinations thereof, including all HSV functions (e.g., to enable propagation of HSV amplicons, which comprise minimal HSV sequences, such as only inverted terminal repeats and the packaging signal or only ITRs and an HSV promoter). The cell line preferably is further characterized in that it contains the complementing genes in a non-overlapping fashion with the HSV vector, which minimizes, and practically eliminates, the possibility of the HSV vector genome recombining with the cellular DNA. Accordingly, the presence of replication competent HSV is minimized, if not avoided in the vector stock, which, therefore, is suitable for certain therapeutic purposes, especially gene therapy purposes. The construction of complementing cell lines involves standard molecular biology and cell culture techniques well known in the art.

When the vector is a replication deficient HSV, the nucleic acid sequence encoding the protein (e.g., a carboxy-amidated peptide) is preferably located in the locus of an essential HSV gene, most preferably either the ICP4 or the ICP27 gene locus of the HSV genome. The insertion of a nucleic acid sequence into the HSV genome (e.g., the ICP4 or the ICP27 gene locus of the HSV genome) can be facilitated by known methods, for example, by the introduction of a unique restriction site at a given position of the HSV genome.

A preferred HSV vector for use in the context of the invention contains expanded ICP4, or ICP27 deletions, and preferably both. By "expanded" deletions in this context, it is meant that the preferred vectors have no homologous sequences at either or both of these loci relative to the complementing cell line used for their production. Desirably, the virus has no remaining ICP4 or ICP27 (or both) coding or promoter sequences. Preferably, the deletion in ICP27 extends as well into the UL55 locus, and desirably both genes are deleted. Thus, a most preferred virus for use in the invention contains extended deletions in ICP4, ICP27 and UL 55 such that there is no viral homology to these genes used in a complementing cell line. Desirably, the vector further does not include any homologous DNA sequences to that employed in the complementing cell line (e.g., even using different regulatory sequences and polyadenylation sequences).

It will be understood that other vectors in addition to HSV vectors can also be used in preparing the gene transfer vectors. For example, adenoviral, adeno-associated viral, and retroviral vectors can be used in the methods and compositions of the present invention. Construction of such vectors is known to those of ordinary skill in the art (see, e.g., U.S. Pat. Nos. 4,797,368, 5,691,176, 5,693,531, 5,880,102, 6,210,393, 6,268,213, 6,303,362, and 7,045,344). Non-viral methods can also be utilized for gene delivery such as gene-gun application of a plasmid encoding precursors of one or more peptides along with other appropriate components such as amino acids 1-99 of preproenkephalin or a signal sequence of another preproprotein described above. Another non-viral method of gene delivery is intrathecal electroporation of a drug regulated expression system. Alternative, implantable cell lines can be engineered to produce the desired peptide or library.

In other embodiments, particularly useful for handling a random or semirandom library of the inventive expression cassettes, the expression cassettes (or library) can be inserted into bacterial artificial chromosome (BAC) phage vectors or plasmids. Such vectors permit amplification of the expression cassette in bacterial systems, which can generate large quantities of the expression cassettes for use in assays. Such vectors can, in fact, contain the genome of a viral vector (e.g., HSV) containing the expression cassette. Such vectors can be efficiently amplified in a bacterial system to generate a large number of viral genomes, which can be introduced into suitable eukaryotic cells to generate viral particles.

Where the vector system includes a random or semirandom library, preferably the vector backbone (e.g., including the vector and the promoter under which the expression cassettes are controlled) are homologous or substantially homologous (allowing for minor sequence variations due to mutations during replication). In this sense, it is preferred for the population of vectors to differ primarily (or exclusively) in the sequences encoding the peptide precursors. In this embodiment, the expression cassettes are within respective gene transfer vectors and under the control of respective promoters within the population of vectors within the vector system.

Where the peptide is a carboxy-amidated peptide that is an agonist of an opioid receptor, the invention further provides a method of treating pain comprising administering the gene transfer vector to a patient. Preferably, the patient is a mammal, such as a rat, mouse, rabbit, cat, dog, horse, cow, pig, or primate. More preferably, the patient is a human. Preferably, the pain is neuropathic pain. In some embodiments, the pain can be associated with inflammation. In other embodiments, the pain can be associated with cancer. In some preferred embodiments, the pain is associated with spinal cord injury.

Suitable methods of administering the inventive vector and composition of the invention to an animal (especially a human) for therapeutic or prophylactic purposes, e.g., gene therapy, vaccination, and the like (see, for example, references 74-77), are available, and, although more than one route can be used to administer the composition, a particular route can provide a more immediate and more effective reaction than another route. A preferred route of administration involves transduction of dorsal root ganglion neurons through peripheral inoculation to result in vector delivery to the dorsal horn. In many embodiments, this can be accomplished by delivering the gene transfer vector by subcutaneous inoculation, which is an attractive feature of the inventive approach. Subcutaneous administration may occur at a location proximate to the dorsal root ganglion or the spinal cord, or at another location at the discretion of the treating clinician, such as a location convenient for administration. In other embodiments, the gene transfer vector can be administered to the dorsal root ganglion of the patient. In still other embodiments, the gene transfer vector can be administered to the spinal cord of the patient.

The method of treating spinal cord injury pain or peripheral neuropathic pain further can comprise the administration (i.e., pre-administration, co-administration, and/or post-administration) of other treatments and/or agents to modify (e.g., enhance) the effectiveness of the method. The method of the invention can further comprise the administration of other substances which locally or systemically alter (i.e., diminish or enhance) the effect of the composition on a host. For example, substances that diminish any systemic effect of the protein produced through expression of the nucleic acid sequence of the vector in a host can be used to control the level of systemic toxicity in the host. Likewise, substances that enhance the local effect of the protein produced through expression of the nucleic acid sequence of the vector in a host can be used to reduce the level of the protein required to produce a prophylactic or therapeutic effect in the host. Such substances include antagonists, for example, soluble receptors or antibodies directed against the protein produced through expression of the nucleic acid sequence of the vector, and agonists of the protein.

It will be observed that, for use in therapy, the gene transfer vector can be formulated into a pharmaceutical composition comprising the vector and a pharmaceutically-acceptable carrier. Any suitable formulation can be used, depending on the desired route of administration (e.g., oral, transdermal, nasal, or injection (e.g., subcutaneous, intravenous, parenteral, intracranial, etc.)). Thus, the gene transfer vector can be formulated into ointments, creams, salves and the like for topical administration. The vector can be formulated as an aerosol (e.g., for administration using a nebulizer) for bronchial delivery. The vector alternatively can be formulated in a suitable buffer (e.g., physiological saline) for injection.

The dose administered to an animal, particularly a human, in the context of the invention will vary with the particular vector, the composition containing the vector and the carrier therefor (as discussed above), the method of administration, and the particular site and organism being treated. The dose should be sufficient to effect a desirable response, e.g., therapeutic or prophylactic response, within a desirable time frame. Thus, the dose of the vector of the inventive composition typically will be about $1 \times 10^5$ or more particle units (e.g., about $1 \times 10^6$ or more particle units, about $1 \times 10^7$ or more particle units, $1 \times 10^8$ or more particle units, $1 \times 10^9$ or more particle units, $1 \times 10^{10}$ or more particle units, $1 \times 10^{11}$ or more particle units, or about $1 \times 10^{12}$ or more particle units). The dose of the vector typically will not be $1 \times 10^{13}$ or less particle units (e.g., $4 \times 10^{12}$ or less particle units, $1 \times 10^{12}$ or less particle units, $1 \times 10^{11}$ or less particle units, or even $1 \times 10^{10}$ or less particle units).

The invention further provides viral stock comprising a plurality of the gene transfer vectors. The stock can have any desired titer of vector, typically measured in plaque forming units (pfu). Typically the stock will have between about $10^5$ pfu/ml to about $10^8$ pfu/ml. In some embodiments, the viral stock can be homogenous. In some embodiments, the DNA sequences encoding precursors of peptides differ between the vectors within the viral stock. In a preferred embodiment, respective DNA sequences encoding precursors of peptides among the vectors within the viral stock define a random or semi-random peptide library. In more preferred embodiments, the peptide precursors encoded in the viral stock are precursors of carboxy amidated peptides.

Where vector system includes a population of vectors defining a random or semirandom library, the invention provides a method for detecting a peptide having a desired effect. In accordance with the method, the population of vectors is introduced into a host cell system under conditions sufficient for the peptides encoded by the expression cassettes to be expressed. Thereafter, the host cell system can be assayed for the desired effect. If desired, assaying the host cell system can be accomplished in comparison with a control agent. The control agent can be an agent known to precipitate the desired effect (positive control) or an agent known not to exhibit the desired effect (negative control). Following the assay, the sequence of the DNA encoding the peptides from the vectors that precipitate the desired effect can be deduced by standard methods.

The host cell system can be in vivo or in vitro. For in vitro application, the assay desirably is conducted in multi-well plates (e.g., 96 well plates), which can facilitate high-throughput screening for the desired effect. For such applications, preferably the expression vector system comprising the library is introduced into the wells at a calculated titer of less than 1 vector per well (typically about 0.5 vectors per well) to minimize the statistical likelihood that more than one vector will transfect or infect the cells. As noted above, in some embodiments, the vector system is a viral system, and in others, it is a plasmid or phage system. Where a plasmid or phage system (e.g., BAC) includes a viral genome, however, the cells within the wells will produce viral particles. Alternatively, the BAC system containing the viral genomes (which comprise the respective expression cassettes and promoters) can be used to transform a larger number of cells, and viral particles rescued. The resultant viral particles then can be used in the assay. For example, if about 10,000 BACs containing HSV backbones that carry the random or semirandom library are introduced into host cells in a 6-well dish, after about 24 hours, about 100,000 viral particles typically can be harvested. These can be employed in the assay. Desirably, about 30,000 viral particles should be used (about three times the number of original vectors) to increase the likelihood that all members of the library are being assayed.

The desired effect to be assayed can be any suitably measurable effect, such as apoptosis, changes in the cell cycle, agonism or antagonism of a cell signalizing pathway, differentiation or dedifferentiation, etc. A preferred example of an effect that can be assayed in accordance with the inventive method is agonism of an opiod receptor (such as a mu opiod receptor). A reporter assay that detects agonism of opioid receptors present in the host cell system can be used to detect those wells in which the opioid receptors have been activated by the carboxy-amidated peptide encoded by the expression cassette within the vector. If desired, a known agonist of an opioid receptor such as EM1 or EM2 can be used as a control. The sequence of the DNA encoding the carboxy-amidated peptides from the cells that exhibit opioid receptor agonism can thereafter be deduced by standard methods.

In some embodiments, the host cell system for screening the libraries can be an animal model, which is particularly suitable when the desired effect to be assayed is behavioral in nature. One such example is analgesia. The analgesic effect can be any detected effect observed in conjunction with, for example, neuropathic pain or inflammatory pain. The analgesic effect can include a decrease in hyperalgesia or allodynia brought on by, for example, an external stimulus or a medical condition. In such embodiments, the library can be clonally expanded into a plurality of random stocks of vectors (each of which is substantially homologous), and the respective stocks introduced into an animal model of pain. The vector DNA from those stocks which decrease the pain response in the animal can then be sequenced to identify the encoded carboxy-amidated peptide that acts as an analgesic agent.

Techniques such as Edman sequencing, amplification and selection, and high-throughput assays can be used to analyze peptide libraries. In combination or as an alternative, libraries can be screened using techniques such as fluorescent tagging of a protein domain, surface plasmon resonance, ELISA based screening, mass spectrometry, or other methods known in the art.

The following examples further illustrate the invention but, of course, should not be construed as in any way limiting its scope.

EXAMPLE 1

This example demonstrates the construction of the vEM2 vector.

An EM-2-EGFP cassette was cloned in a multistep strategy starting with plasmid pEGFP-N1(Clonetech, Mountian View, Calif.). The BglII and BamHI sites of pEGFP-N1 were collapsed using their compatible cohesiveness that also removes the majority of the multi-cloning site. The AseI site was converted into a BglII site by ligation of a BglII linker and the SspII sites were similarly converted into a BglII site. Subsequently, the SnaBI to NheI fragment from plasmid pCMVh-PPE containing the SV40 intron and human PPE signal sequence was cloned into the SnaBI to NheI sites(37). The annealed oligonucleitides End2NheAgeU (CTAGC-CAAAAGGTACCCGTTCTTCGGCAAAAGG-TACCCGTTCTTCGGGAAGAAA ATG (SEQ ID NO:9)) and End2NheAgeL (CCGGCATTTTCTTCCCGAA-GAACGGGTACCTTTTGCCGAAGAACGGG-TACCTTTT GG (SEQ ID NO:10)) coding for a double EM-2 moiety were cloned between the unique NheI and AgeI sites fusing the PPE, EM-2, and EGFP coding regions in frame. The resulting BglII fragment containing the entire expression cassette was cloned into the unique BamHI site of the UL41 targeting plasmid p41(67).

The UL41 targeting EM-2 expression cassette plasmid was recombined into a replication defective HSV backbone, QOZ, a derivative of QOZHG(40). QOZHG was derived from the previously described mutant vectors TOZ.1 and d106(38, 68). d106 and TOZ.1 are deleted for the functions of both the essential ICP4 and ICP27 gene coding sequences rendering these vectors multiply replication defective. The viral IE gene enhancer elements (TAATGARAT (SEQ ID NO:11)) were removed from the IE gene promoters of ICP22 and ICP47 to abrogate their expression in the ICP4 and ICP27 deleted background of d106. In addition, d106 contributed an HCMV:EGFP cassette substituted for the UL54 (ICP27) coding sequence while TOZ.1 contributed an ICP0:lacZ cassette inserted in the UL14 locus of QOZHG. The essential gene deletion vectors were propagated on Vero 7b cells engineered to express the complementing genes ICP4 and ICP27 on virus infection(67). QOZ was created by removal of the HCMV:EGFP cassette within the ICP27 locus of the backbone vector QOZHG(40) by homologous recombination with plasmid pPXE(69). The EM-2-EGFP expression cassette was then recombined into the UL41 locus of QOZ and LacZ negative-EGFP positive, recombinants identified on 7b cells. Isolates were triple plaque purified, expanded, and confirmed by Southern blotting, PCR, and sequencing. Vector stocks of one correct recombinant, vEM2, were produced, aliquoted, and stored at −80° C. (70).

EXAMPLE 2

This example demonstrates the ability of vEM2 to produce, process, and secrete EM-2 in vitro. Studies to detect and confirm the identity of EM-2 were carried out using vEM2 or control (QOZHG) vector-transduced primary rat dorsal root ganglia (DRG) cultures(40).

Production of EM-2 was assayed by transducing primary rat dorsal root ganglia (DRG) cultures with vEM2 or control virus, QOZHG, at one plaque forming unit (PFU)/cell or mock transduced for one hour followed by media change. Transduced DRGs were incubated 37° C./5% $CO_2$ for 24 hours when culture media was replaced with secretion stimulation buffer (85mM NaCl, 60 mM KCl). Following 15 minutes of stimulation, buffer was collected, centrifuged and 100 µl subjected to HPLC. HPLC was performed with a Vydac C18 column with a linear gradient of mobile phases 0.1% trifluoroacetic acid (TFA) in water and 0.085% TFA in acetonitrile. To identify the EM-2 fraction, an EM-2 standard (100 µM, Phoenix Pharmaceuticals, Belmont, Calif.) was assayed and a single elution peak was observed at a retention time of 30.301 minutes. To perform RIA and mass spectroscopy, four corresponding test sample fractions were combined.

Figure 2:
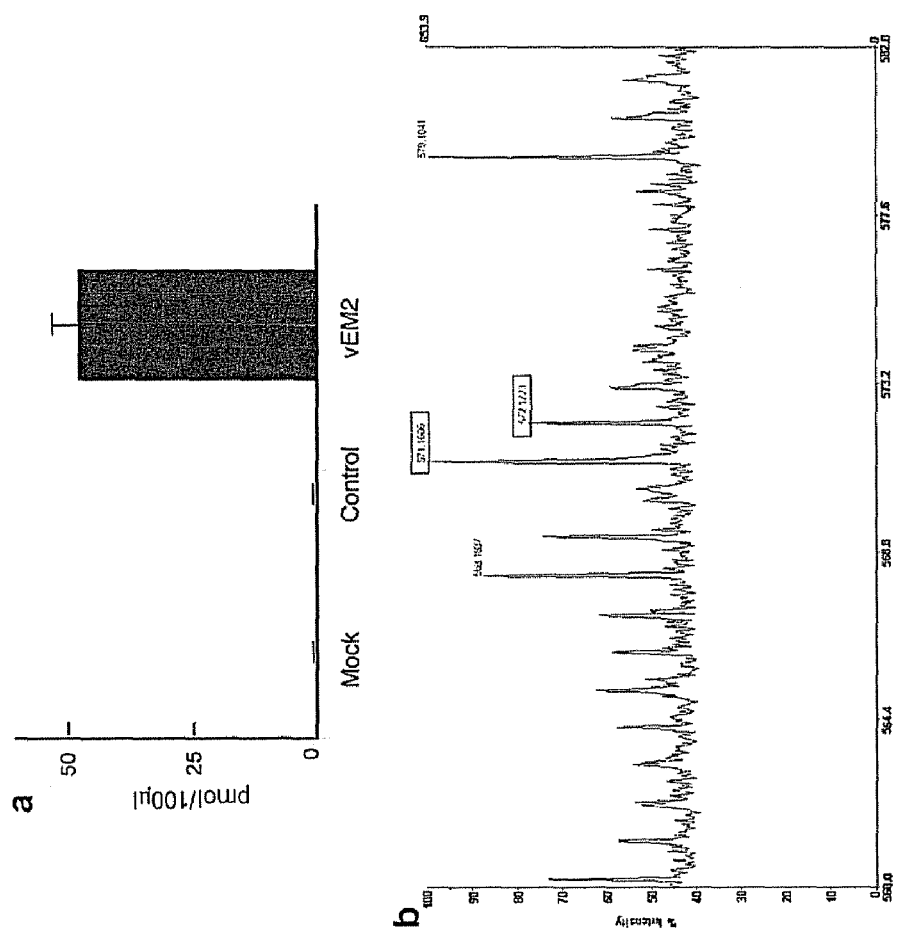
FIG. 2 Detection of EM-2 expression following transduction of rat DRG neurons in vitro. Twenty-four hours after transduction, cultures were incubated in secretion stimulation buffer for fifteen minutes and the supernatant subjected to HPLC. (A) EM-2 HPLC fractions were assayed by RIA for EM-2 expression. EM-2 levels derived from mock-transduced and control vector (QOZHG) vector-transduced neurons were below the level of detection. vEM2 transduced DRGs produced approximately 50 pg EM-2/100 µl stimulation buffer. (B) Mass spectroscopy of the EM-2 HPLC fractions revealed peptides with a mass indistinguishable from EM-2 standard.

Results from EM-2 RIA analyses demonstrated that following treatment of vEM2-transduced DRG neurons with stimulation buffer, approximately 50 pmol EM-2 was released while similarly-treated control vector or mock-transduced neurons showed no appreciable EM-2 signal (FIG. 2A). Mass spectroscopy using in vitro synthesized amidated EM-2 peptide as a positive control confirmed the identity of EM-2 produced from vEM2 transduced DRG neurons (FIG. 2B). Thus, the replication defective HSV vector vEM2 carrying the synthetic EM-2 construct produced and secreted the desired amidated EM-2 peptide product in transduced neurons.

EXAMPLE 3

This example demonstrates the in vivo efficacy of gene-based EM-2 delivery in a model of neuropathic pain, specifically a spinal nerve ligation model. The spinal nerve ligation model was utilized to produce mechanical allodynia and thermal hyperalgesia, hallmarks of neuropathic pain(41).

Male Sprague-Dawley rats weighing 225 to 250 g underwent selective L5 SNL with the approval of the University Committee on Use and Care of Animals(53). Under isoflurane anesthesia, an incision was made in the atlanto-occipital membrane, a polyethylene (PE-10) catheter, filled with 0.9% saline, was advanced 8.5 cm caudally to position its tip at the level of the lumbar enlargement. The rostral tip of the catheter was passed subcutaneously, externalized on top of the skull, and sealed with a stainless-steel plug. One week after implantation of the intrathecal catheter, L5 spinal nerve ligation (SNL) was performed. One week after SNL, 30 µl of vector (either vEM2 or QOZHG, 4×10$^8$ plaque-forming units per milliliter) was injected subcutaneously in the plantar surface of the left hind paw, ipsilateral to the ligation. Ten days after inoculation of vEM2, CTOP (10 micrograms in 10 µl) was injected through the catheter followed immediately by 10 of saline to flush the catheter. Mechanical threshold and thermal hyperalgesia were tested 30 minutes before CTOP and 20 minutes after CTOP.

Mechanical allodynia induced by SNL was determined by assessing the response of paw withdrawal to von Frey hairs of graded tensile strength as described previously with a tactile stimulus producing a 50% likelihood of withdrawal determined using the up-down method(53, 71, 72). Thermal hyperalgesia was determined using a Hargreaves apparatus recording the time to withdrawal from a radiant thermal stimulus positioned directly under the hind paw(73). Parametric statistics, using the general linear model for repeated measures were used to identify significant effects of treatment condition on the behavioral measure of neuropathic pain. The results were examined for a main effect of treatment group.

All statistical analyses were performed using the software package, SPSS 13.0 for Windows (SPSS Inc., Chicago, Ill.).

Figure 3:
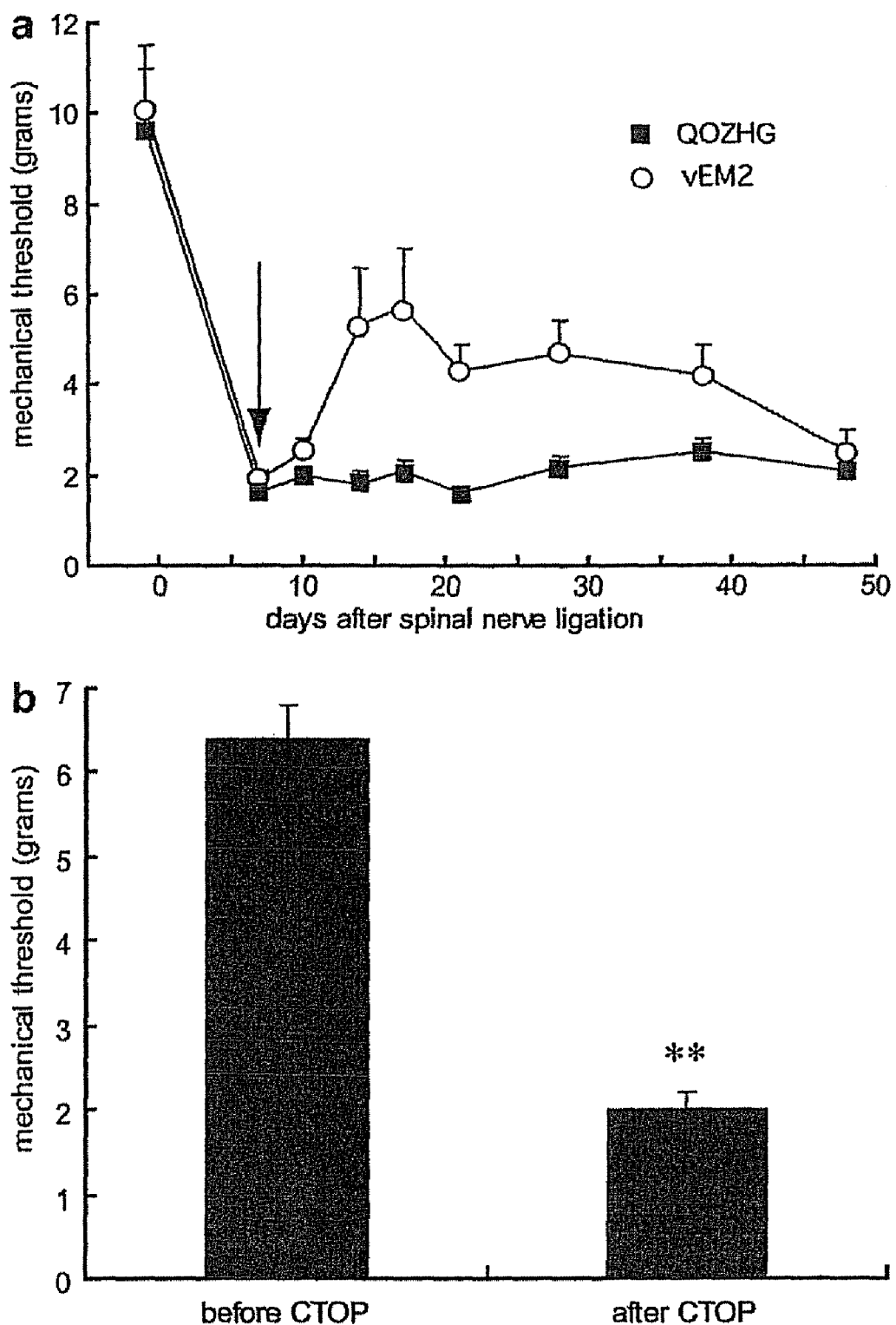
FIG. 3(A) Time course of the antiallodynic effect of vEM2 in neuropathic pain as measured by the mechanical threshold (grams). Results are expressed as mean±standard error of the mean. $P<0.05$ by repeated measures analysis; n=6 animals per group. (B) The antiallodynic effect of endomorphin as measured by the mechanical threshold (grams) produced by vEM2 was reversed by intrathecal injection of CTOP. **$P<0.001$ FIG. 4(A) Antihyperalgesic effect of inoculation of vEM2 1 week after spinal nerve ligation. $P<0.001$ by repeated measures analysis; n=6 animals per group. (B) The antihyperalgesic effect of endomorphin released by vEM2 was reversed by intrathecal injection of CTOP. *$P<0.05$ FIG. 5(A) Time course of the antiallodynic effect of vEM2 in inflammatory pain as measured by the mechanical threshold (grams). *$P<0.05$, $P<0.01$ vs. control vector. (B) The antiallodynic effect of endomorphin as measured by the mechanical threshold (grams) produced by vEM2 was reversed by intrathecal administration of naloxene-methiodide (Nal-M). $P<0.05$ vs. pre Nal-M. (C) The antiallodynic effect of endomorphin as measured by the mechanical threshold (grams) produced by vEM2 was reversed by intraperitoneal administration of naloxene-methiodide (Nal-M). **$P<0.05$ vs. pre Nal-M.
Figure 4:
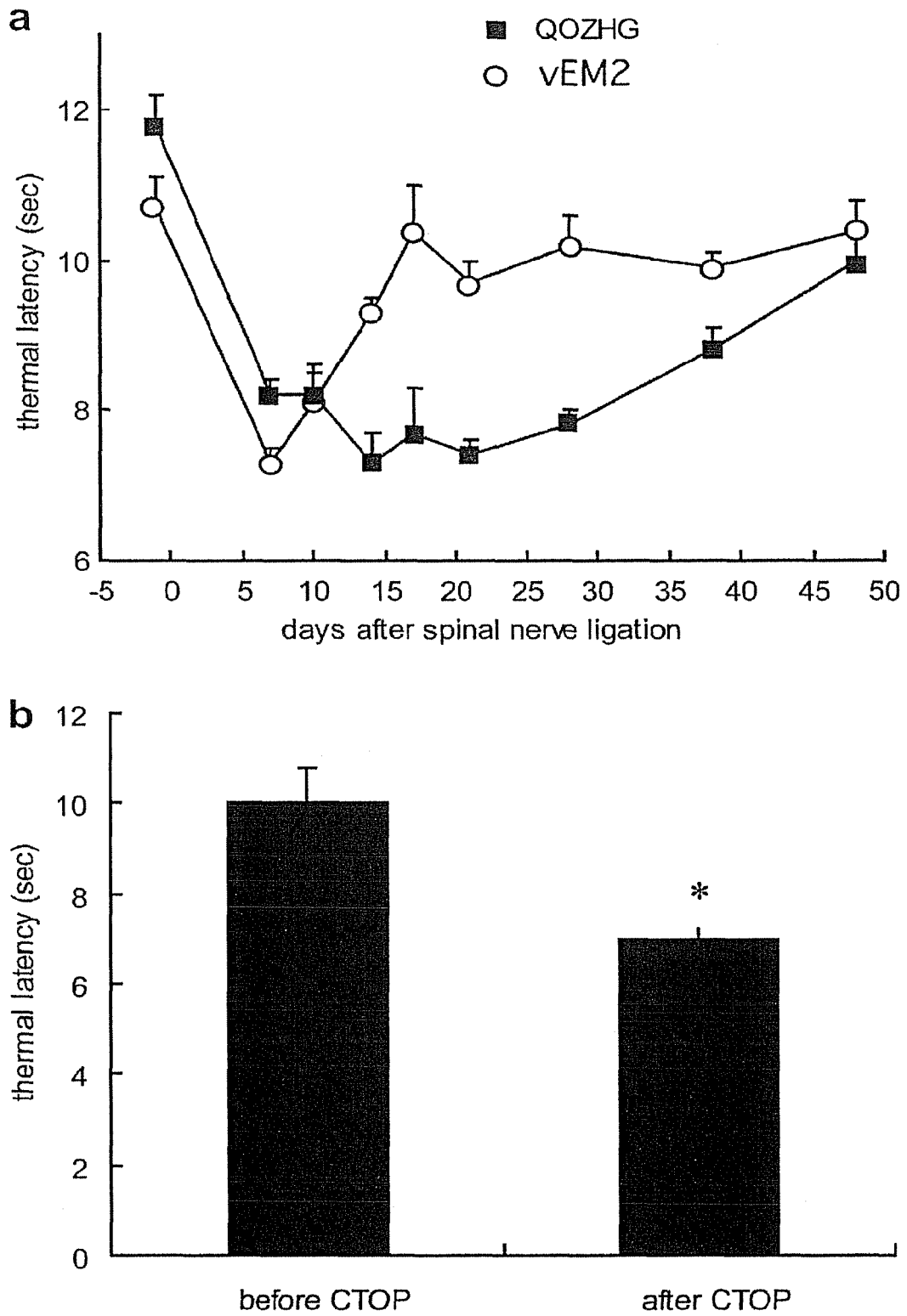

After L5 SNL rats displayed a significant decrease in the magnitude of the mechanical stimulus necessary to evoke a brisk withdrawal response to von Frey hair stimulation (mechanical allodynia, FIG. 3A) and a significant reduction in latency-withdrawal from a heat stimulus (thermal hyperalgesia, FIG. 4A). Rats inoculated with vEM2 showed a statistically significant increase in mechanical threshold compared with control vector (P<0.05). The anti-allodynic effect of vEM2 was sustained and continuous, peaking at 10 days after inoculation (FIG. 3A). By 6 weeks after inoculation the anti-allodynic effect of vEM2 transduction disappeared and the mechanical threshold of vEM2-injected rats was similar to that of controls. Spinal nerve ligation induced a decrease in the thermal latency that lasted 3 weeks before gradually recovering. Rats inoculated with vEM2 showed a statistically significant increase in thermal latency in the ipsilateral paw (P<0.01), an effect that was sustained and continuous (FIG. 4A). In normal animals, intrathecal administration of CTOP alone did not affect the mechanical threshold and thermal latency (data not shown). Ten days after vEM2 in rats with SNL, antiallodynic and antihyperalgesic effects produced by vEM2 were reversed by intrathecal CTOP (FIGS. 3B and 4B).

EXAMPLE 4

This example demonstrates the in vivo efficacy of gene-based EM-2 delivery in a complete Freund's adjuvant (CFA) model of inflammatory pain.

Inflammatory injury was induced by injection of 150 µL CFA in the left-hind paw of male Sprague-Dawley rats. Intrathecal (10 µg) or intraperitoneal (10 mg/kg) naloxone-methiodide (Nal-M), a substituted analogue of naloxone that does not cross the blood-brain barrier was administered three days after CFA injury.

Figure 5:
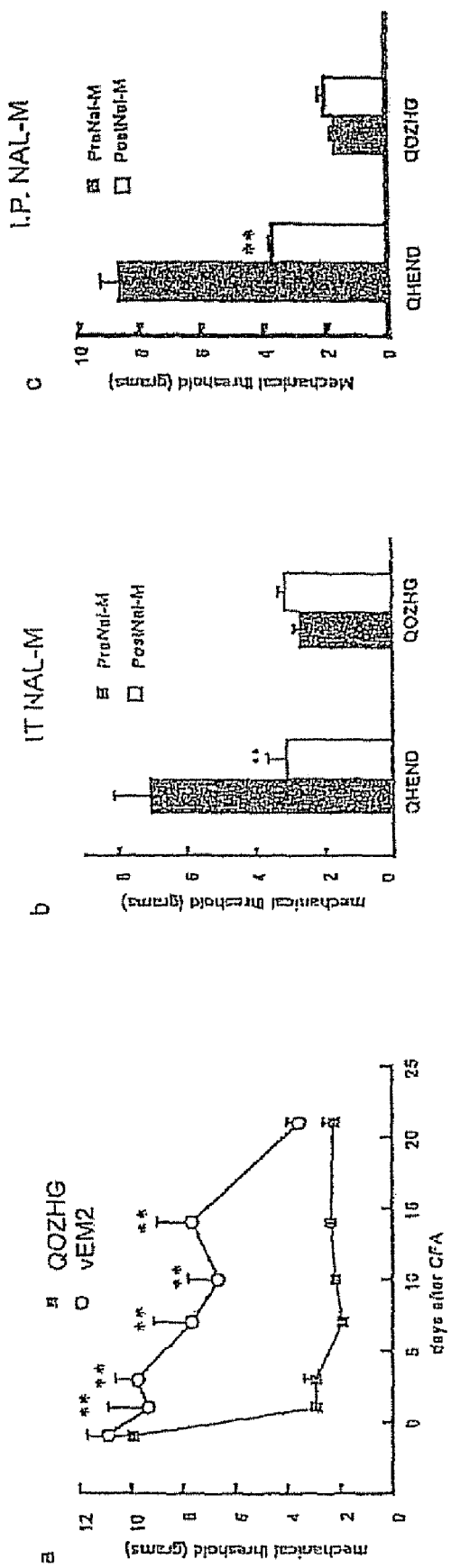

Mechanical allodynia was tested using von Frey hair stimulation as described in Example 2. Subcutaneous inoculation with vEM2 one week prior to CFA injury significantly reduced mechanical allodynia over inoculation with a control (FIG. 5A). The antiallodynic effect of vEM2 was reversed by intrathecal (FIG. 5B) or intraperitoneal (FIG. 5C) administration of Nal-M.

Figure 6:
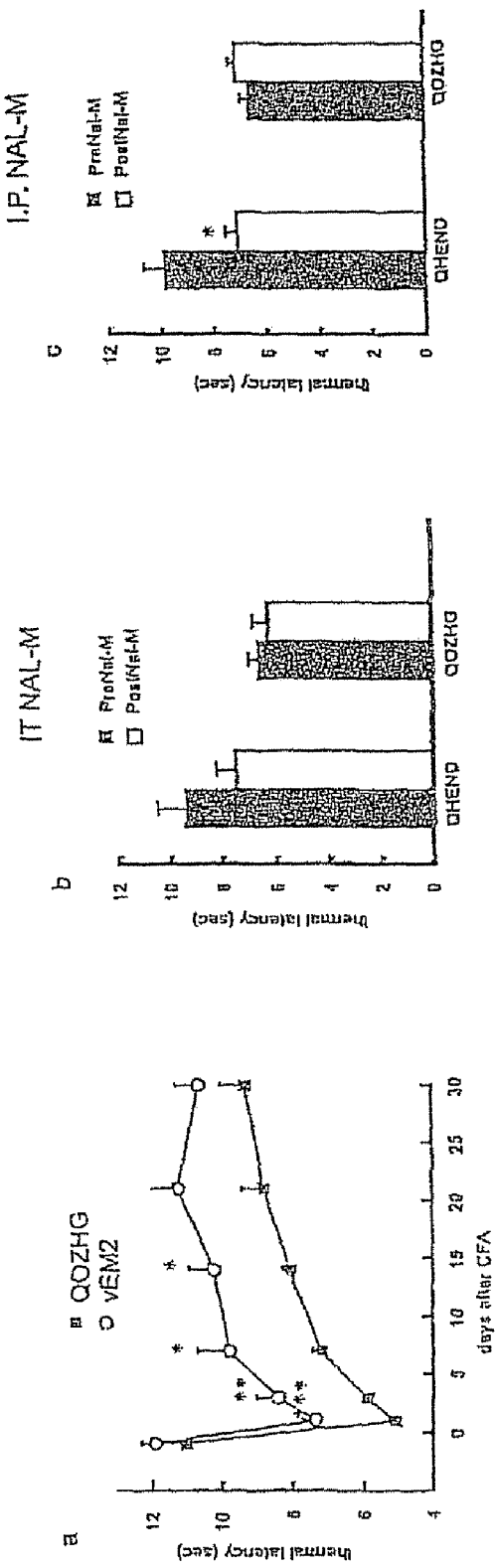
FIG. 6(A) Time course of the antihyperalgesic effect of vEM2 in inflammatory pain as measured by thermal latency (seconds). *$P<0.05$, $P<0.01$, *$P<0.001$ vs. control vector. (B) The antihyperalgesic effect of endomorphin as measured by thermal latency (seconds) produced by vEM2 was not significantly affected by intrathecal administration of naloxene-methiodide (Nal-M). (C) The antihyperalgesic effect of endomorphin as measured by thermal latency (seconds) produced by vEM2 was reversed by intraperitoneal administration of naloxene-methiodide (Nal-M). *$P<0.05$ vs. pre Nal-M.

Thermal hyperalgesia was tested using a Hargreaves apparatus as in Example 2. Subcutaneous inoculation with vEM2 one week prior to CFA injury significantly reduced thermal hyperalgesia over inoculation with a control (FIG. 6A). Intraperitoneal administration of Nal-M reversed the anti-hyperalgesic effect of vEM2 (FIG. 6B), but intrathecal administration of Nal-M did not significantly counteract the effect of vEM2 (FIG. 6C).

Figure 7:
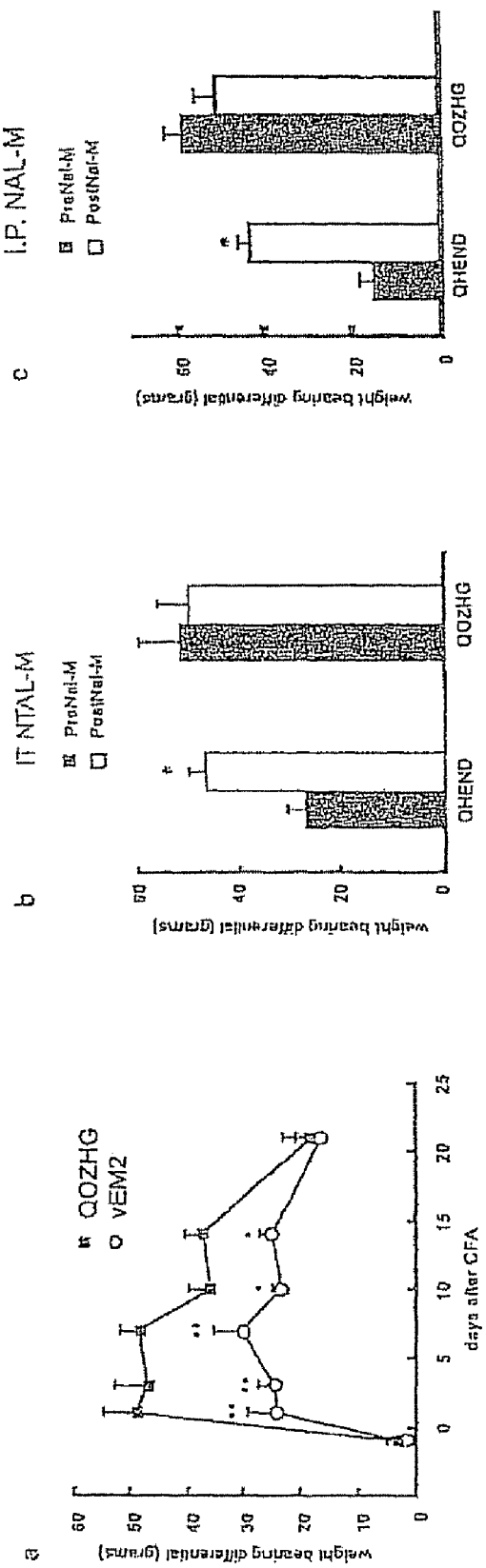
FIG. 7(A) Time course of the antiallodynic effect of vEM2 in inflammatory pain as measured by the weight bearing differential (grams). *$P<0.05$, **$P<0.01$ vs. control vector. (B) The antiallodynic effect of endomorphin as measured by the weight bearing differential (grams) produced by vEM2 was reversed by intrathecal administration of naloxene-methiodide (Nal-M). *P<0.05 vs. pre Nal-M. (C) The antiallodynic effect of endomorphin as measured by the weight bearing differential (grams) produced by vEM2 was reversed by intraperitoneal administration of naloxene-methiodide (Nal-M). *P<0.05 vs. pre Nal-M.

Weight-bearing ability in the CFA model was measured using an incapacitance analgesia meter. Subcutaneous inoculation with vEM2 one week prior to CFA injury significantly reduced the difference in weight bearing over inoculation with a control (FIG. 7A). The effect of vEM2 was reversed by intrathecal (FIG. 7B) or intraperitoneal (FIG. 7C) administration of Nal-M.

Figure 8:
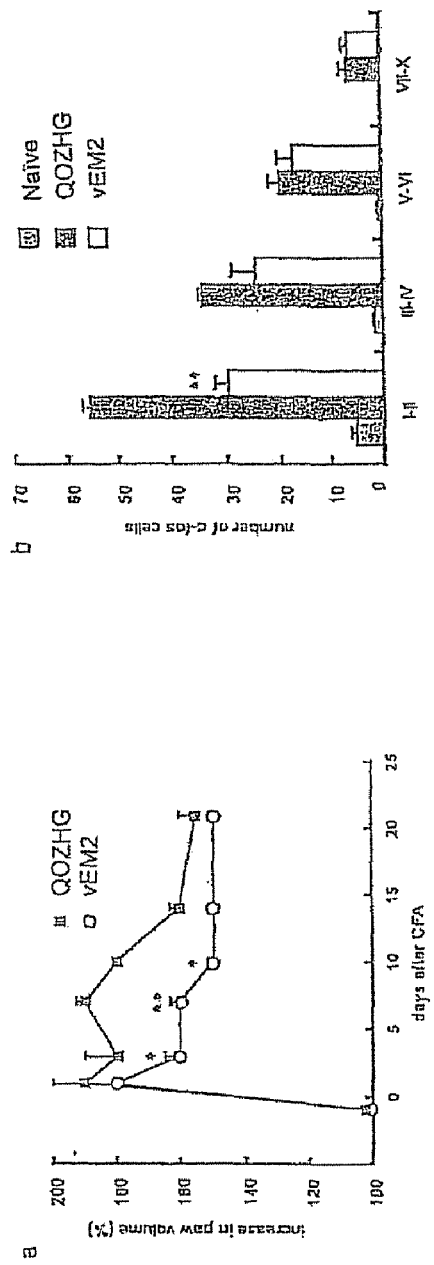
FIG. 8(A) Time course of the anti-inflammatory effect of vEM2 in inflammatory pain as measured by increase in paw volume (%). *P<0.05, P<0.01 vs. control vector. (B) Expression of c-fos cells in laminae I-II of dorsal horn was reduced in animals inoculated with vEM2. P<0.01 vs. control vector.

Paw inflammation was measured using a plethysmometer (paw volume meter). Subcutaneous inoculation with vEM2 one week prior to CFA injury significantly reduced the volume of the injured paw over inoculation with a control (FIG. 8A).

Expression of c-fos in the dorsal horn was evaluated after 10 minutes of gentle touch stimulation to the injured paw administered two hours before sacrifice. Levels of c-fos cells in laminae I-II of the dorsal horn were significantly reduced in animals inoculated with vEM2 (FIG. 8B).

EXAMPLE 5

This example demonstrates the in vivo efficacy of gene-based EM-2 delivery in a formalin model of inflammatory pain.

Inflammatory pain was evaluated using an injection of formalin (50 µL of a 5% solution) into the hind paw of male Sprague-Dawley rats. Injection of formalin induces a biphasic behavioral response, in which animals lick, bite, and flinch the injured paw. The first phase (0-10 minutes after formalin injection) is representative of a short-lasting burst of small afferent activity. The second phase (10-60 minutes after formalin injection) is believed to reflect a state of facilitated processing driven by the moderate ongoing peripheral input. Two hours after the injection of formalin, rats were anesthetized deeply with an overdose of 4% chloral hydrate and perfused through the ascending aorta with 400 mL of 4% paraformaldehyde in PBS.

Figure 9:
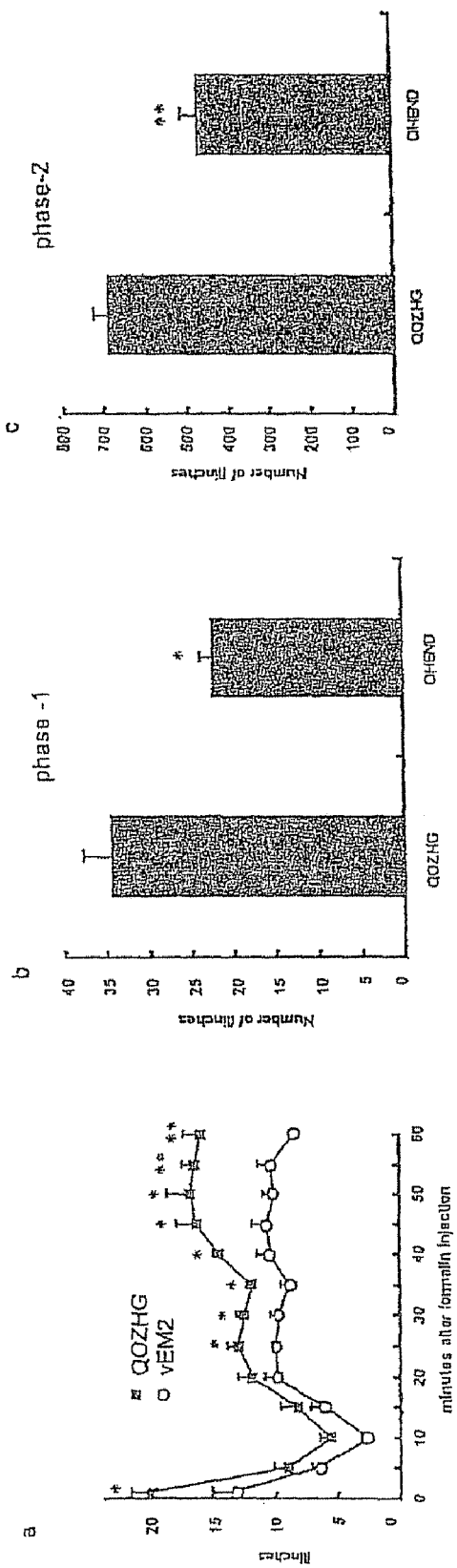
FIG. 9(A) Time course of nocisponsive behavior after administration of formalin as measured by number of flinches. *P<0.05, **P<0.01 vs. control vector. (B) The antinociceptive effect of vEM2 as measured by number of flinches was significant in phase 1 after formalin injection. *P<0.05 vs. control vector. (C) The antinociceptive effect of vEM2 as measured by number of flinches was significant in phase 2 after formalin injection. **P<0.01 vs. control vector.

Administration of vEM2 to the hind paw significantly reduced nocisponsive behavior over administration of a control in the formalin test (FIG. 9A). The sum of the antinociceptive effect of vEM2 was significant in both phases of the formalin test (FIGS. 9B-C).

Figure 10:
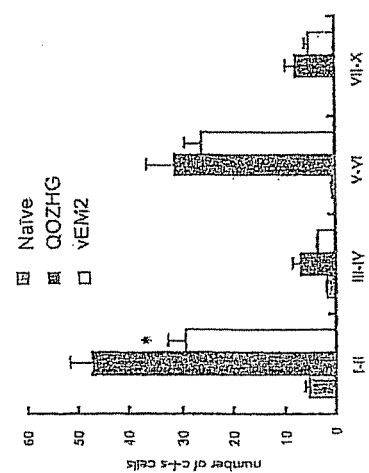
FIG. 10 Expression of c-fos cells in laminae I-II of dorsal horn was reduced after formalin injection in animals inoculated with vEM2. *P<0.05 vs. control vector.

Inoculation of vEM2 one week prior to administration of formalin significantly suppressed expression of c-fos in the spinal dorsal horn laminae I-II (FIG. 10).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCE LIST

1. Bailey, C. P. & Connor, M. (2005) Curr Opin Pharmacol 5, 60-8.
2. Ueda, H. (2004) Ann NY Acad Sci 1025, 376-82.
3. Mayer, D. J., Mao, J., Holt, J. & Price, D. D. (1999) Proc Natl Acad Sci USA 96, 7731-6.
4. McNicol, E., Horowicz-Mehler, N., Fisk, R. A., Bennett, K., Gialeli-Goudas, M., Chew, P. W., Lau, J. & Carr, D. (2003) J Pain 4, 231-56.
5. Eguchi, M. (2004) Med Res Rev 24, 182-212.
6. Zadina, J. E. (2002) Jpn J Pharmacol 89, 203-8.
7. Zadina, J. E., Hackler, L., Ge, L. J. & Kastin, A. J. (1997) Nature 386, 499-502.
8. Julius, D. (1997) Nature 386, 442.
9. Sanderson Nydahl, K., Skinner, K., Julius, D. & Basbaum, A. I. (2004) Eur J Neurosci 19, 1789-99.
10. Smith, R. R., Martin-Schild, S., Kastin, A. J. & Zadina, J. E. (2001) Neuroscience 105, 773-8.
11. Aicher, S. A., Mitchell, J. L., Swanson, K. C. & Zadina, J. E. (2003) Brain Res 977, 190-8.
12. Wang, Q. P., Zadina, J. E., Guan, J. L. & Shioda, S. (2002) Jpn J Pharmacol 89, 209-15.
13. Loh, Y. P., Maldonado, A., Zhang, C., Tam, W. H. & Cawley, N. (2002) Ann NY Acad Sci 971, 416-25.
14. Lledo, P. M. (1997) Eur J Endocrinol 137, 1-9.
15. Hook, V., Yasothornsrikul, S., Greenbaum, D., Medzihradszky, K. F., Troutner, K., Toneff, T., Bundey, R., Logrinova, A., Reinheckel, T., Peters, C. & Bogyo, M. (2004) Biol Chem 385, 473-80.
16. von Eggelkraut-Gottanka, R. & Beck-Sickinger, A. G. (2004) Curr Med Chem 11, 2651-65.
17. Owen, T. C. & Merkler, D. J. (2004) Med Hypotheses 62, 392-400.
18. Ouafik, L. H., Stoffers, D. A., Campbell, T. A., Johnson, R. C., Bloomquist, B. T., Mains, R. E. & Eipper, B. A. (1992) Mol Endocrinol 6, 1571-84.
19. Eipper, B. A., Stoffers, D. A. & Mains, R. E. (1992) Annu Rev Neurosci 15, 57-85.
20. Ronai, A. Z., Szemenyei, E., Kato, E., Kocsis, L., Orosz, G., Al-Khrasani, M. & Toth, G. (2006) Regul Pept 134, 54-60.
21. Finking, R. & Marahiel, M. A. (2004) Annu Rev Microbiol 58, 453-88.
22. Tseng, L. F. (2002) Jpn J Pharmacol 89, 216-20.
23. Janecka, A., Fichna, J., Kruszynski, R., Sasaki, Y., Ambo, A., Costentin, J. & do-Rego, J. C. (2005) Biochem Pharmacol 71, 188-95.
24. Fichna, J., do-Rego, J. C., Kosson, P., Costentin, J. & Janecka, A. (2005) Biochem Pharmacol 69, 179-85.
25. Obara, I., Przewlocki, R. & Przewlocka, B. (2004) Neurosci Lett 360, 85-9.
26. Soignier, R. D., Vaccarino, A. L., Brennan, A. M., Kastin, A. J. & Zadina, J. E. (2000) Life Sci 67, 907-12.
27. Mizoguchi, H., Wu, H. E., Narita, M., Sora, I., Hall, S. F., Uhl, G. R., Loh, H. H., Nagase, H. & Tseng, L. F. (2003) J Pharmacol Sci 93, 423-9.
28. Mizoguchi, H., Wu, H. E., Narita, M., Loh, H. H., Nagase, H. & Tseng, L. F. (2002) Neurosci Lett 335, 91-4.
29. Sora, I., Takahashi, N., Funada, M., Ujike, H., Revay, R. S., Donovan, D. M., Miner, L. L. & Uhl, G. R. (1997) Proc Natl Acad Sci U S A 94, 1544-9.
30. Kastin, A. J., Fasold, M. B., Smith, R. R., Horner, K. A. & Zadina, J. E. (2001) Exp Brain Res 139, 70-5.
31. Soignier, R. D., Vaccarino, A. L., Fanti, K. A., Wilson, A. M. & Zadina, J. E. (2004) Neurosci Lett 366, 211-4.
32. Okada, Y., Tsuda, Y., Bryant, S. D. & Lazarus, L. H. (2002) Vitam Horm 65, 257-79.
33. Janecka, A., Kruszynski, R., Fichna, J., Kosson, P. & Janecki, T. (2006) Peptides 27, 131-5.
34. Chen, J. C., Tao, P. L., Li, J. Y., Wong, C. H. & Huang, E. Y. (2003) Peptides 24, 477-81.
35. Girard, J. P., Baekkevold, E. S., Feliu, J., Brandtzaeg, P. & Amalric, F. (1999) Proc Natl Acad Sci U S A 96, 12772-7.
36. Hofmann, K. & Stoffel, W. (1993) Biol Chem. Hoppe-Seyler 374, 166.
37. Liu, F., Housley, P. R. & Wilson, S. P. (1996) J Neurochem 67, 1457-62.
38. Krisky, D., Wolfe, D., Goins, W., Marconi, P., Ramakrishnan, R., Mata, M., Rouse, R., Fink, D. & Glorioso, J. (1998) Gene Ther 5, 1593-1603.
39. Wolfe, D., Goins, W., Fink, D. & Glorioso, J. (2000) in Gene therapy: Therapeutic mechnisms and strageties., eds. Templeton, N. & Lasic, D. (Marcell Dekker, Inc., New York), Vol. 1, pp. 81-107.
40. Chen, X., Li, J., Mata, M., Goss, J., Wolfe, D., Glorioso, J. C. & Fink, D. J. (2000) J Virol 74, 10132-41.
41. Kim, S. H. & Chung, J. M. (1992) Pain 50, 355-363.
42. Hamman, J. H., Enslin, G. M. & Kotze, A. F. (2005) BioDrugs 19, 165-77.
43. Egleton, R. D. & Davis, T. P. (2005) NeuroRx 2, 44-53.
44. Miljanich, G. P. (2004) Curr Med Chem 11, 3029-40.
45. Bolkenius, F. N. & Ganzhorn, A. J. (1998) Gen Pharmacol 31, 655-9.
46. Przewlocki, R. & Przewlocka, B. (2005) Curr Pharm Des 11, 3013-25.
47. Bennett, G. J. & Xie, Y. K. (1988) Pain 33, 87-107.
48. Seltzer, Z., Dubner, R. & Shir, Y. (1990) Pain 43, 205-18.
49. Gold, M. S. (2000) Pain 84, 117-20.
50. Goss, J. R., Natsume, A., Wolfe, D., Mata, M., Glorioso, J. C. & Fink, D. J. (2004) Methods Mol Biol 246, 309-22.
51. Hao, S., Mata, M., Wolfe, D., Glorioso, J. C. & Fink, D. J. (2005) Ann Neurol 57, 914-8.
52. Liu, J., Wolfe, D., Hao, S., Huang, S., Glorioso, J. C., Mata, M. & Fink, D. J. (2004) Mol Ther 10, 57-66.
53. Hao, S., Mata, M., Goins, W., Glorioso, J. C. & Fink, D. J. (2003) Pain 102, 135-42.
54. Goss, J. R., Harley, C. F., Mata, M., O'Malley, M. E., Goins, W. F., Hu, X., Glorioso, J. C. & Fink, D. J. (2002) Ann Neurol 52, 662-5.
55. Goss, J. R., Mata, M., Goins, W. F., Wu, H. H., Glorioso, J. C. & Fink, D. J. (2001) Gene Ther 8, 551-6.
56. Yeomans, D. C., Lu, Y., Laurito, C. E., Peters, M. C., Vota-Vellis, G., Wilson, S. P. & Pappas, G. D. (2006) Mol Ther 13, 589-97.
57. Meunier, A., Latremoliere, A., Mauborgne, A., Bourgoin, S., Kayser, V., Cesselin, F., Hamon, M. & Pohl, M. (2005) Mol Ther 11, 608-16.
58. Primeaux, S. D., Wilson, M. A., Wilson, S. P., Guth, A. N., Lelutiu, N. B. & Holmes, P. V. (2003) Brain Res 988, 43-55.
59. Braz, J., Beaufour, C., Coutaux, A., Epstein, A. L., Cesselin, F., Hamon, M. & Pohl, M. (2001) J Neurosci 21, 7881-8.
60. Antunes Bras, J. M., Epstein, A. L., Bourgoin, S., Hamon, M., Cesselin, F. & Pohl, M. (1998) J Neurochem 70, 1299-303.
61. Milligan, E. D., Langer, S. J., Sloane, E. M., He, L., Wieseler-Frank, J., O'Connor, K., Martin, D., Forsayeth, J.

R., Maier, S. F., Johnson, K., Chavez, R. A., Leinwand, L. A. & Watkins, L. R. (2005) Eur J Neurosci 21, 2136-48.
62. Milligan, E. D., Sloane, E. M., Langer, S. J., Cruz, P. E., Chacur, M., Spataro, L., Wieseler-Frank, J., Hammack, S. E., Maier, S. F., Flotte, T. R., Forsayeth, J. R., Leinwand, L. A., Chavez, R. & Watkins, L. R. (2005) Mol Pain 1, 9.
63. Xu, Y., Gu, Y., Xu, G. Y., Wu, P., Li, G. W. & Huang, L. Y. (2003) Proc Natl Acad Sci U S A 100, 6204-9.
64. Gu, Y., Xu, Y., Li, G. W. & Huang, L. Y. (2005) J Pain 6, 447-54.
65. Chuang, Y. C., Yang, L. C., Chiang, P. H., Kang, H. Y., Ma, W. L., Wu, P. C., DeMiguel, F., Chancellor, M. B. & Yoshimura, N. (2005) Urology 65, 804-10.
66. Wu, C. M., Lin, M. W., Cheng, J. T., Wang, Y. M., Huang, Y. W., Sun, W. Z. & Lin, C. R. (2004) Gene Ther 11, 933-40.
67. Krisky, D. M., Marconi, P. C., Oligino, T. J., Rouse, R. J., Fink, D. J., Cohen, J. B., Watkins, S. C. & Glorioso, J. C. (1998) Gene Ther 5, 1517-30.
68. Hobbs, W. E., 2nd & DeLuca, N. A. (1999) J Virol 73, 8245-55.
69. Niranjan, A., Wolfe, D., Tamura, M., Soares, M. K., Krisky, D. M., Lunsford, L. D., Li, S., Fellows-Mayle, W., DeLuca, N. A., Cohen, J. B. & Glorioso, J. C. (2003) Mol Ther 8, 530-42.
70. Puskovic, V., Wolfe, D., Goss, J., Huang, S., Mata, M., Glorioso, J. C. & Fink, D. J. (2004) Mol Ther 10, 67-75.
71. Chaplan, S. R., Bach, F. W., Pogrel, J. W., Chung, J. M. & Yaksh, T. L. (1994) J Neurosci Methods 53, 55-63.
72. Dixon, W. J. (1980) Annu Rev Pharmacol Toxicol 20, 441-462.
73. Hargreaves, K., Dubner, R., Brown, F., Flores, C. & Joris, J. (1988) Pain 32, 77-88.
74. Rosenfeld et al., Science, 252, 431-434 (1991)
75. Jaffe et al., Clin. Res., 39(2), 302A (1991)
76. Rosenfeld et al., Clin. Res., 39(2), 311A (1991)
77. Berkner, BioTechniques, 6, 616-629 (1988)
78. Turk, et al., Curr. Opin. Chem. Biol. 7(1):84-90 (2003)

The invention claimed is:

1. A synthetic genetic expression cassette comprising:
   (a) a first DNA sequence consisting of a DNA sequence encoding amino acids 1-99 of human preproenkephalin;
   (b) a second DNA sequence encoding a precursor of a peptide flanked by cleavage sites, wherein the second DNA sequence is not endogenous human enkephalin; and
   (c) optionally a third DNA sequence encoding a biomarker protein; wherein the first, second, and optional third DNA sequence are in frame relative to each other.

2. The synthetic expression cassette of claim 1, wherein the peptide is a carboxy-amidated peptide.

3. The synthetic expression cassette of claim 1, comprising two or more DNA sequences encoding precursors of peptides, wherein each DNA sequence encoding a precursor of a peptide is flanked by cleavage sites.

4. The synthetic expression cassette of claim 1, wherein the peptide is a cyclic peptide.

5. The synthetic expression cassette of claim 1 or 3, wherein the cleavage sites are selected from the group consisting of dibasic cleavage sites, furin cleavage sites, or carboxypeptidase cleavage sites.

6. The synthetic expression cassette of claim 1, wherein the cleavage sites are dibasic cleavage sites.

7. The synthetic expression cassette of claim 1, wherein the precursor of a peptide comprises between two and twenty amino acids.

8. The expression cassette of claim 2, wherein a precursor of a carboxy-amidated peptide comprises a carboxy-terminal glycine residue.

9. The synthetic expression cassette of claim 1, wherein the peptide is an agonist of an opioid receptor.

10. A library comprising a plurality of synthetic expression cassettes of claim 1.

11. A gene transfer vector comprising the synthetic expression cassette of claim 1 or 2 under the control of a promoter.

12. A library comprising a plurality of gene transfer vectors of claim 11.

13. A gene transfer vector comprising the synthetic expression cassette of claim 11 under the control of a promoter, wherein the peptide is an agonist of an opioid receptor.

14. A pharmaceutical composition comprising the gene transfer vector of claim 11 and a pharmaceutically acceptable carrier.

15. The expression cassette of claim 1, wherein the second DNA sequence encodes a precursor of endomorphin-1 or endomorphin-2.

* * * * *

SEQUENCE LISTING

```
<160> NUMBER OF SEQ ID NOS: 11

<210> SEQ ID NO 1
<211> LENGTH: 99
<212> TYPE: PRT
<213> ORGANISM: Homo sapiens

<400> SEQUENCE: 1

Met Ala Arg Phe Leu Thr Leu Cys Thr Trp Leu Leu Leu Leu Gly Pro
1               5                   10                  15

Gly Leu Leu Ala Thr Val Arg Ala Glu Cys Ser Gln Asp Cys Ala Thr
            20                  25                  30

Cys Ser Tyr Arg Leu Val Arg Pro Ala Asp Ile Asn Phe Leu Ala Cys
        35                  40                  45

Val Met Glu Cys Glu Gly Lys Leu Pro Ser Leu Lys Ile Trp Glu Thr
    50                  55                  60

Cys Lys Glu Leu Leu Gln Leu Ser Lys Pro Glu Leu Pro Gln Asp Gly
65                  70                  75                  80

Thr Ser Thr Leu Arg Glu Asn Ser Lys Pro Glu Glu Ser His Leu Leu
                85                  90                  95

Ala Lys Arg

<210> SEQ ID NO 2
<211> LENGTH: 58
<212> TYPE: PRT
<213> ORGANISM: Homo sapiens

<400> SEQUENCE: 2

Met Lys Ile Leu Val Ala Leu Ala Val Phe Phe Leu Val Ser Thr Gln
1               5                   10                  15

Leu Phe Ala Glu Glu Ile Gly Ala Asn Asp Asp Leu Asn Tyr Trp Ser
            20                  25                  30

Asp Trp Tyr Asp Ser Asp Gln Ile Lys Glu Glu Leu Pro Glu Pro Phe
        35                  40                  45

Glu His Leu Leu Gln Arg Ile Ala Arg Arg
    50                  55

<210> SEQ ID NO 3
```

```
<211> LENGTH: 25
<212> TYPE: PRT
<213> ORGANISM: Homo sapiens

<400> SEQUENCE: 3

Met Pro Arg Ser Cys Cys Ser Arg Ser Gly Ala Leu Leu Leu Ala Leu
1               5                   10                  15

Leu Leu Gln Ala Ser Met Glu Val Arg
            20                  25

<210> SEQ ID NO 4
<211> LENGTH: 55
<212> TYPE: PRT
<213> ORGANISM: Homo sapiens

<400> SEQUENCE: 4

Met Glu Ile Ile Ser Ser Lys Leu Phe Ile Leu Leu Thr Leu Ala Thr
1               5                   10                  15

Ser Ser Leu Leu Thr Ser Asn Ile Phe Cys Ala Asp Glu Leu Val Met
            20                  25                  30

Ser Asn Leu His Ser Lys Glu Asn Tyr Asp Lys Tyr Ser Glu Pro Arg
        35                  40                  45

Gly Tyr Pro Lys Gly Glu Arg
    50                  55

<210> SEQ ID NO 5
<211> LENGTH: 4
<212> TYPE: PRT
<213> ORGANISM: Artificial
<220> FEATURE:
<223> OTHER INFORMATION: Synthetic

<400> SEQUENCE: 5

Tyr Pro Trp Phe
1

<210> SEQ ID NO 6
<211> LENGTH: 4
<212> TYPE: PRT
<213> ORGANISM: Artificial
<220> FEATURE:
<223> OTHER INFORMATION: Synthetic

<400> SEQUENCE: 6

Tyr Pro Phe Phe
1

<210> SEQ ID NO 7
<211> LENGTH: 5
<212> TYPE: PRT
<213> ORGANISM: Artificial
<220> FEATURE:
<223> OTHER INFORMATION: Synthetic

<400> SEQUENCE: 7

Tyr Pro Trp Phe Gly
1               5

<210> SEQ ID NO 8
<211> LENGTH: 5
<212> TYPE: PRT
<213> ORGANISM: Artificial
<220> FEATURE:
<223> OTHER INFORMATION: Synthetic
```

-continued

```
<400> SEQUENCE: 8

Tyr Pro Phe Phe Gly
1               5

<210> SEQ ID NO 9
<211> LENGTH: 57
<212> TYPE: DNA
<213> ORGANISM: Artificial
<220> FEATURE:
<223> OTHER INFORMATION: Synthetic

<400> SEQUENCE: 9
ctagccaaaa ggtacccgtt cttcggcaaa aggtacccgt tcttcgggaa gaaaatg      57

<210> SEQ ID NO 10
<211> LENGTH: 57
<212> TYPE: DNA
<213> ORGANISM: Artificial
<220> FEATURE:
<223> OTHER INFORMATION: Synthetic

<400> SEQUENCE: 10
ccggcatttt cttcccgaag aacgggtacc ttttgccgaa gaacgggtac cttttgg      57

<210> SEQ ID NO 11
<211> LENGTH: 9
<212> TYPE: DNA
<213> ORGANISM: Artificial
<220> FEATURE:
<223> OTHER INFORMATION: Synthetic

<400> SEQUENCE: 11 taatgarat                                                            9
```